(12) United States Patent
Haas et al.

(10) Patent No.: US 10,329,590 B2
(45) Date of Patent: Jun. 25, 2019

(54) METHOD OF PRODUCING NYLON

(71) Applicant: Evonik Degussa GmbH, Essen (DE)

(72) Inventors: Thomas Haas, Münster (DE);
Eva-Maria Eckl, Marl (DE); Simon Beck, Münster (DE)

(73) Assignee: Evonik Degussa GmbH, Essen (DE)

( * ) Notice: Subject to any disclaimer, the term of this patent is extended or adjusted under 35 U.S.C. 154(b) by 38 days.

(21) Appl. No.: 15/309,951

(22) PCT Filed: May 5, 2015

(86) PCT No.: PCT/EP2015/059786
§ 371 (c)(1),
(2) Date: Nov. 9, 2016

(87) PCT Pub. No.: WO2015/173059
PCT Pub. Date: Nov. 19, 2015

(65) Prior Publication Data
US 2017/0260553 A1    Sep. 14, 2017

(30) Foreign Application Priority Data
May 13, 2014    (EP) .................................... 14168174

(51) Int. Cl.
*C12P 13/00*    (2006.01)
*C12P 13/02*    (2006.01)
*C08G 69/08*    (2006.01)

(52) U.S. Cl.
CPC ............ *C12P 13/001* (2013.01); *C08G 69/08* (2013.01); *C12P 13/005* (2013.01); *C12P 13/02* (2013.01); *C12Y 101/99* (2013.01); *C12Y 114/15003* (2013.01); *C12Y 206/01062* (2013.01)

(58) Field of Classification Search
None
See application file for complete search history.

(56) References Cited

U.S. PATENT DOCUMENTS

| | | | |
|---|---|---|---|
| 3,992,268 A | 11/1976 | Antos | |
| 4,540,772 A | 9/1985 | Pipper et al. | |
| 5,604,127 A | 2/1997 | Nisbet et al. | |
| 5,723,603 A | 3/1998 | Gilbert et al. | |
| 5,807,722 A | 9/1998 | Gaddy | |
| 7,196,218 B2 | 3/2007 | Gaddy et al. | |
| 7,241,908 B2 | 7/2007 | Haas et al. | |
| 7,364,718 B2 | 4/2008 | Haas et al. | |
| 8,241,881 B2 | 8/2012 | Bradin | |
| 8,535,921 B2 | 9/2013 | Kohn et al. | |
| 8,703,451 B2 | 4/2014 | Haas et al. | |
| 8,809,576 B2 | 8/2014 | Schraven et al. | |
| 8,835,691 B2 | 9/2014 | Klasovsky et al. | |
| 8,999,684 B2 | 4/2015 | Poetter et al. | |
| 9,012,227 B2 | 4/2015 | Karau et al. | |
| 9,068,202 B2 | 6/2015 | Tran et al. | |
| 9,102,958 B2 | 8/2015 | Botes et al. | |
| 9,150,890 B2 | 10/2015 | Poetter et al. | |
| 9,200,043 B2 | 12/2015 | Poetter et al. | |
| 9,249,435 B2 | 2/2016 | Gielen et al. | |
| 9,562,930 B2 | 2/2017 | Makuth et al. | |
| 9,580,732 B2 | 2/2017 | Poetter et al. | |
| 9,587,231 B2 | 3/2017 | Hom et al. | |
| 9,677,045 B2 | 6/2017 | Pharkya et al. | |
| 2007/0092957 A1 | 4/2007 | Donaldson et al. | |
| 2007/0275447 A1 | 11/2007 | Lewis et al. | |
| 2008/0057554 A1 | 3/2008 | Huhnke et al. | |
| 2010/0137641 A1 | 6/2010 | Iida et al. | |
| 2010/0324257 A1 | 12/2010 | Karau et al. | |
| 2011/0111475 A1 | 5/2011 | Kuhry et al. | |
| 2011/0118433 A1 | 5/2011 | Poetter et al. | |
| 2011/0171702 A1 | 7/2011 | Reinecke et al. | |
| 2012/0034665 A1 | 2/2012 | Haas et al. | |
| 2012/0045807 A1 | 2/2012 | Simpson et al. | |
| 2013/0189750 A1 | 7/2013 | Jin et al. | |
| 2013/0203953 A1 | 8/2013 | Pereira et al. | |
| 2014/0011249 A1 | 1/2014 | Burgard et al. | |
| 2014/0051136 A1 | 2/2014 | Liao et al. | |
| 2014/0120587 A1 | 5/2014 | Haas et al. | |

(Continued)

FOREIGN PATENT DOCUMENTS

| | | |
|---|---|---|
| CA | 2 900 293 | 8/2014 |
| GB | 1009370 | 11/1965 |

(Continued)

OTHER PUBLICATIONS

International Search Report for PCT/EP2015/059786 (international counterpart of U.S. Appl. No. 15/309,951), filed May 5, 2015.
Written Opinion of the International Searching Authority for PCT/EP2015/059786 (international counterpart of U.S. Appl. No. 15/309,951), filed May 5, 2015.
International Preliminary counterpart of Report on Patentability for PCT/EP2015/059786 (international couterpart of U.S. Appl. No. 15/309,951), filed May 5, 2015.
European Search Report for EP 14 16 8174 (European counterpart of U.S. Appl. No. 15/309,951), filed May 13, 2014.

(Continued)

*Primary Examiner* — Suzanne M Noakes
(74) *Attorney, Agent, or Firm* — Law Office of: Michael A. Sanzo, LLC

(57) ABSTRACT

There is provided a method of producing aminohexanoic acid and/or aminohexanoic acid ester from synthesis gas, the method comprising:
A. contacting the synthesis gas with at least one bacteria capable of carrying out the Wood-Ljungdahl pathway and the ethanol-carboxylate fermentation to produce hexanoic acid; and
B. contacting the hexanoic acid with a genetically modified cell to produce aminohexanoic acid and/or aminohexanoic acid ester, wherein the genetically modified cell has an increased activity, in comparison with its wild type, of alkane monooxygenase, alcohol dehydrogenase, and ω-transaminase.

15 Claims, 6 Drawing Sheets
Specification includes a Sequence Listing.

(56) References Cited

U.S. PATENT DOCUMENTS

| | | |
|---|---|---|
| 2014/0178948 A1 | 6/2014 | Schaffer et al. |
| 2014/0186905 A1 | 7/2014 | Schaffer et al. |
| 2014/0256904 A1 | 9/2014 | Schaffer et al. |
| 2014/0308717 A1 | 10/2014 | Haas et al. |
| 2015/0010968 A1 | 1/2015 | Engel et al. |
| 2015/0044744 A1 | 2/2015 | Pfeffer et al. |
| 2015/0093798 A1 | 4/2015 | Jung et al. |
| 2015/0099282 A1 | 4/2015 | Haas et al. |
| 2015/0111253 A1 | 4/2015 | Schaffer et al. |
| 2015/0111254 A1 | 4/2015 | Hennemann et al. |
| 2015/0125912 A1 | 5/2015 | Haas et al. |
| 2015/0218600 A1 | 8/2015 | Haas et al. |
| 2015/0267231 A1 | 9/2015 | Haas et al. |
| 2015/0275245 A1 | 10/2015 | Haas et al. |
| 2015/0284747 A1 | 10/2015 | Schiemann et al. |
| 2015/0299741 A1 | 10/2015 | Engel et al. |
| 2015/0353963 A1 | 12/2015 | Haas et al. |
| 2016/0138058 A1 | 5/2016 | Wittmann et al. |
| 2016/0138061 A1 | 5/2016 | Haas et al. |
| 2016/0177259 A1 | 6/2016 | Haas et al. |
| 2016/0215302 A1 | 7/2016 | Haas et al. |
| 2016/0215304 A1 | 7/2016 | Haas et al. |
| 2016/0244790 A1 | 8/2016 | Haas et al. |
| 2016/0272950 A1 | 9/2016 | Corthals et al. |
| 2016/0326549 A1 | 11/2016 | Dennig et al. |
| 2016/0326555 A1 | 11/2016 | Engel et al. |
| 2017/0183694 A1 | 6/2017 | Pharkya et al. |
| 2017/0204437 A1 | 7/2017 | Haas et al. |
| 2017/0233777 A1* | 8/2017 | Botes .................... C12P 7/40 528/323 |
| 2017/0260552 A1 | 9/2017 | Haas et al. |
| 2018/0208947 A1 | 7/2018 | Haas et al. |

FOREIGN PATENT DOCUMENTS

| | | |
|---|---|---|
| GB | 1113357 | 5/1968 |
| GB | 1563933 | 4/1980 |
| WO | WO 98/00558 | 1/1998 |
| WO | WO 00/20566 | 4/2000 |
| WO | WO 00/68407 | 11/2000 |
| WO | WO 2007/136762 | 11/2007 |
| WO | WO 2008/119082 | 10/2008 |
| WO | WO 2008/148640 | 12/2008 |
| WO | WO 2009/078973 | 6/2009 |
| WO | WO 2009/100434 | 8/2009 |
| WO | WO 2010/118410 | 10/2010 |
| WO | WO 2012/099603 | 7/2012 |
| WO | WO 2012/177943 | 12/2012 |
| WO | WO 2015/110518 | 7/2015 |
| WO | WO 2015/172972 | 11/2015 |
| WO | WO 2016/008925 | 1/2016 |
| WO | WO 2016/008979 | 1/2016 |
| WO | WO 2016/131801 | 8/2016 |
| WO | WO 2016/184656 | 11/2016 |
| WO | WO 2016/184663 | 11/2016 |
| WO | WO 2017/001170 | 1/2017 |

OTHER PUBLICATIONS

European Search Opinion for EP 14 16 8174 (European counterpart of U.S. Appl. No. 15/309,951), filed May 13, 2014.
International Search Report for PCT/EP2015/058469 (international counterpart of copending U.S. Appl. No. 15/309,994), filed Apr. 20, 2015.
Written Opinion of the International Searching Authority for PCT/EP2015/058469 (international counterpart of copending U.S. Appl. No. 15/309,994), filed Apr. 20, 2015.
International Preliminary counterpart of Report on Patentability for PCT/EP2015/058469 (international counterpart of copending U.S. Appl. No. 15/309,994), filed Apr. 20, 2015.
European Search Report for EP 14 16 8130 (European counterpart of copending U.S. Appl. No. 15/309,994), filed May 13, 2014.
European Search Opinion for EP 14 16 8130 (European counterpart of copending U.S. Appl. No. 15/309,994), filed May 13, 2014.
U.S. Appl. No. 15/309,994, filed Nov. 9, 2016, Haas.
U.S. Appl. No. 15/326,546, filed Jan. 16, 2017, Haas.
U.S. Appl. No. 15/326,552, filed Jan. 16, 2017, Haas.
Abrini, et al., "*Clostridium autoethanogenum*, sp. nov., an anaerobic bacterium that produces ethanol from carbon monoxide," *Arch Microbiol* 161(4):345-351 (Apr. 1994).
Andreesen, et al., "Fermentation of Glucose, Fructose, and Xylose by *Clostridium thermoaceticum*: Effect of Metals on Growth Yield, Enzymes, and the Synthesis of Acetate from CO2," *Journal of Bacteriology* 114(2):743-751 (May 1973).
Baba, et al., "Construction of *Escherichia coli* K-12 in-frame, single gene knockout mutants: the Keio collection," *Molecular Systems Biology* 21:1-11 (Feb. 2006).
Becker, et al., "A generic system for the *Escherichia coli* cell-surface display of lipolytic enzymes," *FEBS Letters* 575(5):1177-1182 (Feb. 2005).
Bornstein, et al., "The energy metabolism of *Clostridium Kluyveri* and the synthesis of fatty acids," *J Biol Chem* 172(2):659-669 (Feb. 1948).
Byoung, et al., "In situ extractive fermentation for the production of hexanoic acid from galactitol by *Clostridium* sp. BS-1," *Enzyme and Microbial Technology* 53(3)143-151 (Aug. 2013).
Cotter, et al., "Ethanol and acetate production by *Clostridium ljungadahlii* and *Clostridium autoethanogenum* using resting cells," *Bioprocess Biosyst Eng* 32(3):369-380 (Apr. 2009).
Dar, et al., "Competition and coexistence of sulfate-reducing bacteria, acetogens and methanogens in a lab-scale anaerobic bioreactor as affected by changing substrate to sulfate ratio," *Appl Microbiol Biotechnol* 78(6):1045-1055 (Feb. 2008).
De Lorenzo, et al., "Mini-Tn5 Transposon Derivatives for Insertion Mutagenesis, Promoter Probing, and Chromosomal Insertion of Cloned DNA in Gram-Negative Eubacteria," *Journal of Bacteriology* 172(11):6568-6572 (Nov. 1990).
Demler, et al., "Reaction Engineering Analysis of Hydrogenotrophic Production of Acetic Acid by *Acetobacterium woodii*," *Biotechnology and Bioengineering* 108(2):470-474 (Feb. 2011).
Ding, et al., "Caproate formation in mixed-culture fermentative hydrogen production," *Bioresource Technology* 101(24):9550-9559 (Dec. 2010).
Kaulmann, et al., "Substrate spectrum of ω-transaminase from *Chromobacteria violaceum* DSM30191 and its potential for biocatalysis," *Enzyme and Microbial Technology* 41(5):628-637 (Oct. 2007).
Kenealy, et al., "Studies on the substrate range of *Clostridium Kluyveri*; the use of propanol and succinate," *Arch Microbiol* 141(3):187-194 (Apr. 1985).
Kieun, et al., "In situ Biphasic Extractive Fermentation for Hexanoic Acid Production from Sucrose by *Megasphaera elsdenii* NCIMB 702410," *Appl Biochem Biotechnol* 171(5):1094-1107 (Nov. 2013).
Kojima, et al., "Purification and Characterization of the Lipase from *Pseudomonas fluorescens* HU380," *Journal of Bioscience and Bioengineering* 96(3):219-226 (accepted May 2003).
Levy, et al., "Biorefining of biomass to liquid fuels and organic chemicals," *Enzyme and Microbial Technology* 3(3):207-215 (Jul. 1981).
Levy, et al., "Kolbe Electrolysis of Mixtures of Aliphatic Organic Acids," *Journal of the Electrochemical Society* 131(4):773-777 (Apr. 1984).
Mieke, et al., "Bioelectrochemical Production of Caproate and Caprylate from Acetate by Mixed Cultures," *ACS Sustainable Chem Eng* 1(5):513-518 (May 2013).
Li, a dissertation, "Production of Acetic Acid from Synthesis Gas with Mixed Acetogenic Microorganisms," Texas A & M University, Chemical Engineering (May 2002).
Morinaga, et al., "The production of acetic acid from carbon dioxide and hydrogen by an anaerobic bacterium," *Journal of Biotechnology* 14(2):187-194 (May 1990).
Overkamp, et al., "Cloning and characterization of eight cytochrome P450 cDNAs from chickpea (*Cicer arietnum* L.) cell suspension cultures," *Plant Science* 155(1):101-108 (Jun. 2000).

(56) References Cited

OTHER PUBLICATIONS

Panke, et al., "Engineering of a Stable Whole-Cell Biocatalyst Capable of (S)-Styrene Oxide Formation for Continuous Two-Liquid-Phase Applications," *Applied and Environmental Microbiology* 65(12):5619-5623 (Dec. 1999).
Riesenberg, et al., "High cell density fermentation of recombinant *Escherichia coli* expressing human interferon alpha 1," *Appl Microbiol Biotechnol* 34(1):77-82 (accepted Jun. 1990).
Sakai, et al., "Ethanol production from $H_2$ and $CO_2$ by a newly isolated thermophilic bacterium, *Moorella* sp. HUC22-1," *Biotechnology Letters* 26(20):1607-1612 (Oct. 2004).
Saxena, et al., "Effect of trace metals on ehtanol production from synthesis gas by the ethanologenic acetogen, *Clostridium ragsdalei*," *J Ind Microbiol Biotechnol* 38(4):513-521 (accepted Jul. 2010).
Scheps, et al., "Regioselective ωhydroxylation of medium-chain η-alkanes and primary alcohols by CYP153 emxymes from *Mycobacterium marinum* and *Polaromonas* sp. strain JS666," *Organic & Biomolecular Chemistry* 9:6727-6733 (Oct. 2011).
Schmidt, et al., "Production of Acetic Acid from Hydrogen and Carbon Dioxide by *Clostridium* Species ATCC 29797," *Chem Eng Commun* 45(1-6):61-73 (May 1986).
Seedorf, et al., "The genome of *Clostridium Kluyveri*, a strict anaerobe with unique metabolic features," *Proc Natl Acad Sci USA* 105(6):2128-2133 (Feb. 2008).
Seedorf, et al., "*Clostridium Kluyveri* DSM 555 complete genome," retrieved from GenBank, database accession number CP0000673, (Jan. 2014).
Sim, et al., "Optimization of acid production from systhesis gas by chemolithotrophic bacterium—*Clostridium aceticum* using statistical approach," *Bioresource Technology* 99(8):2724-2735 (May 2008).
Smits, et al., "Functional Analysis of Alkane Hydroxylases from Gram-Negative and Gram-Positive Bacteria," *Journal of Bacteriology* 184(6):1733-1742 (Mar. 2002).
Stadtman, et al., "Fatty Acid Synthesis by Enzyme Preparations of *Clostridium Kluyveri*," *J Biol Chem* 184(2):769-794 (Jun. 1950).
Stadtman, et al., "Tracer Experiments on the Mechanism of Synthesis of Valeric and Caproic Acids by *Clostridium Kluyveri*," *J Bio Chem* 178(2):677-682 (Jun. 1948).
Steinbusch, et al., "Biological formation of caproate and caprylate from acetate: fuel and chemical production from low grade biomass," *Energy and Environmental Science* 4:216-224 (accepted Oct. 2010).
Van Beilen, et al., "Diversity of Alkane Hydroxylase Systems in the Environment," *Oil & Gas Science and Technology* 58(4):427-440 (2003).
Vaysse, et al., "Chain-length selectivity of various lipases during hydrolysis, esterification and alcoholysis in biphasic aqueous medium, *Enzyme and Microbial Technology* 31(5):648-655 (Oct. 2002).
Vega, et al., "Study of Gaseous Substrate Fermentations: Carbon Monoxide Conversion to Acette. 1. Batch Culture," *Biotechnology and Bioengineering* 34(6):774-784 (Sep. 1989).
Wadhawan, et al., "Biphasic sonselectrosynthesis. A review," *Pure Appl Chem* 73(12):1947-1955 (Apr. 2001).
Wood, et al., "Life with Co or $CO_2$ and $H_2$ as a source of carbon energy," *FASEB J* 5(2):156-163 (Feb. 1991).
Wu, et al., "Microbial composition and characterization of prevalent methanogens and acetogens isolated from syntrophic methanogenic granules," *Appl Microbiol Biotechnol* 38(2):282-290 (Nov. 1992).
Younesi, et al., "Ethanol and acetate production from synthesis gas via fermentation processes using anaerobic bacterium, *Clostridium ljungadahlii*," *Biochemical Engineering Journal* 27(2):110-119 (Dec. 2005).
Zhang, et al., "Fatty acids production from hydrogen and carbon dioxide by mixed culture in the biofilm reactor," *Water Research* 47(16):6122-6129 (available online Jul. 2013).
Anderlund, et al., "Expression of the *Escherichia coli* pntA and pntB Genes, Encoding Nicotinamide Nucleotide Transhydrogenase, in *Saccharomyces cerevisiae* and Its Effect on Product Formation during Anaerobic Glucose Fermentation," *Appl. Environ. Microbiol.* 65(6):2333-2340 (Jun. 1999).
Devos, et al., "Practical Limits of Function Prediction," *Proteins: Structure, Function and Genetics* 41:98-107 (2000).
Fukaya, et al., "The aarC Gene Responsible for Acetic Acid Assimilation Confers Acetic Acid Resistance on *Acetobacter aceti*," *Journal of Fermentation and Bioengineering* 76(4):270-275 (Jan. 1993).
Hatefi, et al., "Dehydrogenase and transhydrogenase properties of the soluble NADH dehydrogenase of bovine heart mitochondria," *Proc. Natl. Acad. Sci. USA* 74(3):846-850 (Mar. 1977).
Kisselev, "Polypeptide Release Factors in Prokaryotes and Eukaryotes: Same Function, Different Structure," *Structure* 10:8-9 (Jan. 2002).
Mullins, et al., "A Specialized Citric Acid Cycle Requiring Succinyl-Coenzyme A (CoA):Acetate CoA-Transferase (AarC) Confers Acetic Acid Resistance on the Acidophile *Acetobacter aceti*," *Journal of Bacteriology* 190(14):4933-4940 (Jul. 2008).
Perez, et al., "Biocatalytic Reduction of Short-Chain Carboxylic Acids Into Their Corresponding Alcohols With Syngas Fermentation," *Biotechnology and Bioengineering* 110(4):1066-1077 (Apr. 2013).
Stadtman, et al., "Discussion," *Federation Proceedings* 12(3):692-693 (Sep. 1953).
Stadtman, "The Coenzyme A Transphorase System in *Clostridium kluyveri*," *J. Biol. Chem.* 203(1):501-512 (Jul. 1953).
Whisstock, et al., "Prediction of protein function from protein sequence and structure," *Quarterly Reviews of Biophysics* 36(3):307-340 (Aug. 2003).
Witkowski, et al., "Conversion of a β-Ketoacyl Synthase to a Malonyl Decarboxylase by Replacement of the Active-Site Cysteine with Glutamine," *Biochemisty* 38(36):11643-11650 (Sep. 1999).
U.S. Appl. No. 16/063,256, filed Jun. 16, 2018, Haas.

* cited by examiner

```
                       SEQUENCE LISTING

<160> NUMBER OF SEQ ID NOS: 9

<210> SEQ ID NO 1
<211> LENGTH: 1203
<212> TYPE: DNA
<213> ORGANISM: Pseudomonas oleovorans
<220> FEATURE:
<221> NAME/KEY: misc_feature
<223> OTHER INFORMATION: alkane monooxygenase

<400> SEQUENCE: 1
cttgagaaac acagagttct ggattccgct ccagagtacg tagataaaaa gaaatatctc      60
tggatactat caactttgtg gccggctact ccgatgatcg gaatctggct tgcaaatgaa     120
actggttggg ggatttttta tgggctggta ttgctcgtat ggtacggcgc acttccattg     180
cttgatgcga tgtttggtga ggactttaat aatccgcctg aagaagtggt gccgaaacta     240
gagaaggagc ggtactatcg agttttgaca tatctaacag ttcctatgca ttacgctgca     300
ttaattgtgt cagcatggtg ggtcggaact cagccaatgt cttggcttga aattggtgcg     360
cttgccttgt cactgggtat cgtgaacgga ctagcgctca atacaggaca cgaactcggt     420
cacaagaagg agacttttga tcgttggatg gccaaaattg tgttggctgt cgtagggtac     480
```

```
ggtcacttct ttattgagca taataagggt catcaccgtg atgtcgctac accgatggat      540
cctgcaacat cccggatggg agaaagcatt tataagtttt caatccgtga gatcccagga      600
gcatttattc gtgcttgggg gcttgaggaa caacgccttt cgcgccgtgg ccaaagcgtt      660
tggagtttcg ataatgaaat cctccaacca atgatcatca cagttattct ttacgccgtt      720
ctccttgcct tgtttggacc taagatgctg gtgttcctgc cgattcaaat ggctttcggt      780
tggtggcagc tgaccagtgc gaactatatt gaacattacg gcttgctccg tcaaaaaatg      840
gaggacggtc gatatgagca tcaaaagccg caccattctt ggaatagtaa tcacatcgtc      900
tctaatctag tgctgttcca ccttcagcgg cactcggatc accacgcgca tccaacacgt      960
tcttatcagt cacttcggga ttttcccggc ctgccggctc ttccgacggg ttaccctggt     1020
gcatttttga tggcgatgat tcctcagtgg tttagatcag ttatggatcc caaggtagta     1080
gattgggctg gtggtgacct aataagatc caaattgatg attcgatgcg agaaacctat      1140
ttgaaaaaat ttggcactag tagtgctggt catagttcga gtacctctgc ggtagcatcg     1200
tag                                                                   1203
```

<210> SEQ ID NO 2
<211> LENGTH: 1656
<212> TYPE: DNA
<213> ORGANISM: Pseudomonas oleovorans
<220> FEATURE:
<221> NAME/KEY: misc_feature
<223> OTHER INFORMATION: AlkJ gene

<400> SEQUENCE: 2

```
atgtacgact atataatcgt tggtgctgga tctgcaggat gtgtgcttgc taatcgtctt       60
tcggccgacc cctctaaaag agtttgttta cttgaagctg gccgcgaga tacgaatccg       120
ctaattcata tgccgttagg tattgctttg cttcaaata gtaaaagtt gaattgggct       180
tttcaaactg cgccacagca aaatctcaac ggccggagcc ttttctggcc acgaggaaaa       240
acgttaggtg gttcaagctc aatcaacgca atggtctata tccgagggca tgaagacgat       300
taccacgcat gggagcaggc ggccggccgc tactggggtt ggtaccgggc tcttgagttg       360
ttcaaaaggc ttgaatgcaa ccagcgattc gataagtccg agcaccatgg ggttgacgga       420
gaattagctg ttagtgattt aaaatatatc aatccgctta gcaaagcatt cgtgcaagcc       480
ggcatggagg ccaatattaa tttcaacgga gatttcaacg gcgagtacca ggacggcgta       540
gggttctatc aagtaaccca aaaaatgga caacgctgga gctcggcgcg tgcattcttg       600
cacggtgtac tttccagacc aaatctagac atcattactg atgcgcatgc atcaaaaatt       660
cttttttgaag accgtaaggc ggttggtgtt tcttatataa agaaaaatat gcaccatcaa      720
gtcaagacaa cgagtggtgg tgaagtactt cttagtcttg gcgcagtcgg cacgcctcac       780
cttctaatgc tttctggtgt tggggctgca gccgagctta aggaacatgg tgtttctcta       840
gtccatgatc ttcctgaggt ggggaaaaat cttcaagatc atttggacat acattgatg       900
tgcgcagcaa attcgagaga gccgataggt gttgctcttt ctttcatccc tcgtggtgtc       960
tcgggttgt tttcatatgt gtttaagcgc gaggggtttc tcactagtaa cgtggcagag      1020
tcgggtggtt ttgtaaaaag ttctcctgat cgtgatcggc caatttgca gtttcatttc      1080
cttccaactt atcttaaaga tcacggtcga aaaatagcgg gtggttatgg ttatacgcta      1140
catatatgtg atcttttgcc taagagccga ggcagaattg gcctaaaaag cgccaatcca      1200
ttacagccgc ctttaattga cccgaactat cttagcgatc atgaagatat taaaaccatg      1260
```

```
attgcgggta ttaagatagg gcgcgctatt ttgcaggccc catcgatggc gaagcatttt      1320
aagcatgaag tagtaccggg ccaggctgtt aaaactgatg atgaaataat cgaagatatt      1380
cgtaggcgag ctgagactat ataccatccg gtaggtactt gtaggatggg taaagatcca      1440
gcgtcagttg ttgatccgtg cctgaagatc cgtgggttgg caaatattag agtcgttgat      1500
gcgtcaatta tgccgcactt ggtcgcgggt aacacaaacg ctccaactat tatgattgca      1560
gaaaatgcgg cagaaataat tatgcggaat cttgatgtgg aagcattaga ggctagcgct      1620
gagtttgctc gcgagggtgc agagctagag ttggca                               1656
```

<210> SEQ ID NO 3
<211> LENGTH: 1380
<212> TYPE: DNA
<213> ORGANISM: Chromobacterium violaceum
<220> FEATURE:
<221> NAME/KEY: misc_feature
<223> OTHER INFORMATION: omega-transaminase

<400> SEQUENCE: 3

```
atgcagaaac agcgtaccac ctctcagtgg cgtgaactcg atgcggcgca tcatctccat       60
ccgtttaccg ataccgcgag cctcaatcag gcgggtgcgc gtgtgatgac ccgtggcgaa      120
ggcgtgtatc tctgggatag cgaaggcaac aaaattattg atggcatggc gggcctctgg      180
tgcgtgaacg tgggctatgg ccgtaaagat tttgcggaag cggcgcgtcg tcagatggaa      240
gaactcccgt tttataacac cttctttaaa accaccccatc cggcggtggt ggaactcagc      300
agcctcctcg ccgaagttac cccggcaggt tttgatcgtg tgttttatac caacagcggc      360
agcgaaagcg tggataccat gattcgtatg gtgcgtcgtt attgggatgt gcagggcaaa      420
ccggaaaaaa aaccctcat ggccgttgg aacggctatc acggcagcac cattggcggt      480
gcgagcctcg gcggcatgaa atatatgcat gaacagggcg atctcccgat tccgggcatg      540
gcgcatattg aacagccgtg gtggtataaa catggcaaag atatgacccc ggatgaattt      600
ggcgtggttg cggcgcgttg gctcgaagaa aaaattctcg aaatcggcgc ggataaagtg      660
gcggcgtttg tgggcgaacc gattcagggt gcgggcggtg tgattgttcc gccggcaacc      720
tattggccgg aaattgaacg tatttgccgc aaatatgatg tgctcctcgt tgcggatgaa      780
gtgatttgcg gctttggccg taccggcgaa tggtttggcc atcagcattt tggctttcag      840
ccggacctct ttaccgcggc gaaaggcctc agcagcggct atctcccgat ggcgcggtg      900 tttgtgggca aacgtgttgc ggaaggtctc attgcgggcg gtgatttaa ccatggcttt      960 acctatagcg gccatccggt gtgtgcggcg gtggcgcatg cgaatgttgc ggcgctccgt     1020
gatgaaggca ttgtgcagcg tgtgaaagat gatattggcc cgtatatgca gaaacgttgg     1080
cgtgaaacct ttagccgttt tgaacatgtg gatgatgtgc gtggcgtggg catggtgcag     1140
gcgtttaccc tcgtgaaaaa caaagcgaaa cgtgaactct tccggatttt ggcgaaatt      1200 ggcacccctct gccgcgatat ttttttttcgc aacaacctca ttatgcgtgc gtgcggcgat     1260
cacattgtgt ctgcaccgcc gctcgttatg acccgtgcgg aagtggatga atgctcgcc      1320 gtggcggaac gttgcctcga agaatttgaa cagacccctca aagcgcgtgg cctcgcctaa     1380
```

<210> SEQ ID NO 4
<211> LENGTH: 1158
<212> TYPE: DNA
<213> ORGANISM: Pseudomonas sp.
<220> FEATURE:
<221> NAME/KEY: misc_feature
<223> OTHER INFORMATION: PCR amplification of the fragment alkT

<400> SEQUENCE: 4

```
atggcaatcg ttgttgttgg cgctggtaca gctggagtaa atgctgcgtt ctggcttcgt      60
caatatggtt ataaagggga aattaggatt tttagcaggg agtctgtggc gccttatcag     120
cggcctcctc tatccaaggc ttttctgaca agtgagattc agaatccgc agtgccatta      180
aagccagaag gtttttatac gaataacaat attaccattt cgttaaatac accgattgta     240
tcaatcgacg tggggcgtaa gatagtttct tctaaagatg gaaaagaata cgcgtatgaa     300
aaattgattc ttgcaacacc tgctagcgca cgtaggttaa cctgcgaggg gtctgaactg     360
tctggggtct gctatttacg cagtatggaa gacgccaaaa atttacgtag gaaacttgtg     420
gagagtgcgt ctgttgttgt gttgggcggc ggagtaatcg ggcttgaagt cgcctcagct     480
gcggtgggct tagggaagag ggtcacagtg atagaagcca ccccgcgtgt aatggcgcgc     540
gtggttacgc cggcagcagc aaacttagtc agagcccgcc tggaggctga aggaattgag     600
ttcaagctga atgcgaaatt aacgtctata aagggcagga atggccatgt tgaacaatgc     660
gtacttgaaa gtggagaaga aattcaggcg gatctgattg tagttggaat cggtgctatc     720
ccagagctag agctggcaac tgaggcggcc cttgaagtga gtaatggtgt tgtggtcgat     780
gatcagatgt gtacatcgga tacaagtata tatgcaatcg gcgactgcgc aatggctaga     840
aatccttttt ggggaacgat ggtacgttta gagacaattc ataatgcggt tacacacgct     900
caaattgtcg caagtagcat ctgtggcaca tcaacaccag caccaacccc accacggttc     960
tggtctgatc ttaaagggat ggcgctgcaa ggacttggtg ctctaaagga ctacgataaa    1020
ctcgttgttg caattaataa cgaaactctt gaactagaag tccttgcgta caagcaggag    1080
cgactgattg caactgagac aataaatttg cctaaacgtc aaggtgcgct tgcagggagt    1140
ataaaattac ctgattag                                                  1158
```

<210> SEQ ID NO 5
<211> LENGTH: 35
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<223> OTHER INFORMATION: alkBFG forward

<400> SEQUENCE: 5

```
aagggaattc catatgcttg agaaacacag agttc                                35
```

<210> SEQ ID NO 6
<211> LENGTH: 35
<212> TYPE: DNA
<213> ORGANISM: Artificial Sequence
<220> FEATURE:
<223> OTHER INFORMATION: primer sequence
<220> FEATURE:
<221> NAME/KEY: misc_feature
<223> OTHER INFORMATION: alkBFG reverse

<400> SEQUENCE: 6

```
aaaattcgcg tcgacaagcg ctgaatgggt atcgg                                35
```

<210> SEQ ID NO 7
<211> LENGTH: 20
<212> TYPE: DNA
<213> ORGANISM: Artificial Sequence
<220> FEATURE:

```
<223> OTHER INFORMATION: Primer sequence
<220> FEATURE:
<221> NAME/KEY: misc_feature
<223> OTHER INFORMATION: alkT forward

<400> SEQUENCE: 7
tgagacagtg gctgttagag                                                   20

<210> SEQ ID NO 8
<211> LENGTH: 35
<212> TYPE: DNA
<213> ORGANISM: Artificial Sequence
<220> FEATURE:
<223> OTHER INFORMATION: primer sequence
<220> FEATURE:
<221> NAME/KEY: misc_feature
<223> OTHER INFORMATION: alkT reverse

<400> SEQUENCE: 8
taataaccgc tcgagaacgc ttaccgccaa cacag                                  35

<210> SEQ ID NO 9
<211> LENGTH: 519
<212> TYPE: DNA
<213> ORGANISM: Pseudomonas sp.
<220> FEATURE:
<221> NAME/KEY: misc_feature
<223> OTHER INFORMATION: alk gene cluster

<400> SEQUENCE: 9
atggctagct ataaatgccc ggattgtaat tatgtttatg atgagagtgc gggtaatgtg       60
catgaggggt tttctccagg tacgccttgg caccttattc ctgaggattg gtgctgcccc      120
gattgcgccg ttcgagacaa gcttgacttc atgttaattg agagcggcgt aggtgaaaag      180
ggcgtcacct caacccatac ttcgccaaat ttatccgagg ttagtggcac aagtttaact      240
gctgaagcag tggttgcgcc gacaagctta gagaaattgc ctagtgccga cgttaaaggc      300
caagatctat ataaaactca acctccaagg tctgatgccc aaggcgggaa agcatacttg      360
aagtggatat gtattacttg tggccatata tatgatgagg cgttgggcga tgaggccgag      420
ggttttactc caggtactcg ctttgaggat attcctgatg actggtgctg tccggattgc      480
ggggctacga aagaagacta tgtgctctac gaggaaaag                             519
```

METHOD OF PRODUCING NYLON

CROSS REFERENCE TO RELATED APPLICATIONS

The present application is US national stage of international application PCT/EP2015/059786, which had an international filing date of May 5, 2015, and which was published in English on Nov. 19, 2015. Priority is claimed to European application EP 14168174.2, filed on May 13, 2014. The contents of the priority application is hereby incorporated by reference in its entirety.

SUMMARY OF THE INVENTION

The present invention relates to the biotechnological production of polyamides, in particular nylon from synthesis gas which is converted to hexanoic acid and then chemically converted to methyl hexanoate which is then contacted with cells that convert the methyl hexanoate to aminohexanoic acid and/or esters thereof.

BACKGROUND OF THE INVENTION

Polyamides are synthetic polymers where the repeating units (monomers) possess the amide group as a characteristic feature. The designation "polyamides" is usually used to designate synthetic, commercially usable thermoplastics and therefore demarcates this class of substances from the chemically related proteins. Nearly all the important polyamides are derived from primary amines, i.e. the functional group —CO—NH— occurs in their repeat units. Polyamides of secondary amines (—CO—NR—, R=organic residue) also exist. Aminocarboxylic acids, lactams and/or diamines and dicarboxylic acids in particular find application as monomers for the polyamides.

When the repeating units between the amide linkages are substantially aliphatic, they form polyamide polymers that are called nylon. Nylon is known to be made through the condensation reaction between a diamine and a diacid. Nylon is one of the most widely used polymers because of its characteristics. In particular, nylon is highly resilient and durable. Nylon fibres are thus used in many applications, including clothes fabrics, package paper, carpets, musical strings, pipes, rope, mechanical parts and the like.

Some commonly available nylon polymers include but are not limited to nylon 6,6, nylon 6, nylon 11, nylon 12, nylon 4,6, nylon 6,12, nylon 6,10 and the like. Out of which, nylon 6,6 and nylon 6 are the more commonly used polymers. Nylon may be made through step-growth polymerisation or chain-growth polymerisation. Making nylon from a diamine and a diacid or an amino acid is a step-growth polymerisation whereas making nylon from lactams usually involves a chain-growth polymerisation. Since the latter method starts off with monomers, the monomers quickly form high molecular weight polymers making the process of polymerisation more efficient. This method also reduces the formation of intermediate dimers, trimers, and other oligomers. This method is thus more favoured than step-growth polymerisation.

Caprolactam is the feedstock in the production of nylon 6 using chain-growth polymerisation. The production of caprolactam is usually carried out by reacting cyclohexanone with hydrogensulphate or hydrochloride of hydroxylamine resulting in the formation of cyclohexanone oxime. This is then converted by a Beckmann rearrangement into caprolactam, often with the use of concentrated sulphuric acid as catalyst. The raw material, cyclohexanone is usually produced by catalytic oxidation of cyclohexane with oxygen of the air and cyclohexane is in turn obtained by hydrogenation of benzene.

There are several disadvantages with the currently available methods of producing nylon. One disadvantage in the production of lactams by Beckmann rearrangement of oximes is, among other things, that large amounts of salts, for example sodium sulphate, are formed as by-product, which requires disposal. Other methods for the production of lactams described in the prior art which use a different method include EP0748797 which describes a method of production of lactams from dinitriles, in which the dinitrile is hydrogenated to aminonitrile and the aminonitrile is converted by cyclizing hydrolysis to the lactam. Molecular sieves, such as acid zeolites, silicates and non-zeolitic molecular sieves, metal phosphates and metal oxides or mixed metal oxides were used as catalyst for cyclizing hydrolysis. However, this method has, among other drawbacks, the disadvantage that the selectivity of the conversion of the aminonitrile by cyclizing hydrolysis is rather low and therefore large amounts of by-products are also formed.

Further, the traditional manufacture of nylon uses petroleum based intermediates. For example, cyclohexane is used to make adipic acid and caprolactam. Butadiene and natural gas are important raw materials for making hexamethylene diamine. Nylon 12 is also dependent upon butadiene feedstocks. Thus, in most methods of producing lactams described in the prior art, hydrocarbons such as benzene or butadiene are used, and these are obtained by cracking gasoline or petroleum which is bad for the environment. Also, since the costs for these starting materials will be linked to the price of petroleum, with the expected increase in petroleum prices in the future, nylon prices may also increase relative to the increase in the petroleum prices.

Accordingly, it is desirable to find more sustainable raw materials, other than purely petroleum based, as starting materials for nylon production which also cause less damage to the environment.

DESCRIPTION OF THE INVENTION

There is provided a method of producing aminohexanoic acid and/or aminohexanoic acid ester from synthesis gas, the method comprising:
   A. contacting the synthesis gas with at least one acetogenic bacteria and/or hydrogen oxidising bacteria to produce hexanoic acid; and
   B. contacting the hexanoic acid with a genetically modified cell to produce aminohexanoic acid and/or aminohexanoic acid ester, wherein the genetically modified cell has an increased activity, in comparison with its wild type, of at least one enzyme selected from the group consisting of alkane monooxygenase, alcohol dehydrogenase, and ω-transaminase.

In particular, according to any aspect of the present invention, there is provided a method of producing aminohexanoic acid and/or aminohexanoic acid ester from synthesis gas, the method comprising:
   A. contacting the synthesis gas with at least one bacteria capable of carrying out the Wood-Ljungdahl pathway and/or the ethanol-carboxylate fermentation to produce hexanoic acid; and
   B. contacting the hexanoic acid with a genetically modified cell to produce aminohexanoic acid and/or aminohexanoic acid ester, wherein the genetically modified cell has an increased activity, in comparison with its wild type, of alkane monooxygenase, alcohol dehydrogenase, and ω-transaminase.

Usually, a portion of the synthesis gas obtained from the gasification process is first processed in order to optimize product yields, and to avoid formation of tar. Cracking of the undesired tar and CO in the synthesis gas may be carried out using lime and/or dolomite. These processes are described in detail in for example, Reed, 1981.

The synthesis gas may be converted to hexanoic acid in the presence of at least one acetogenic bacteria and/or hydrogen oxidising bacteria. In particular, any method known in the art may be used. Hexanoic acid may be produced from synthesis gas by at least one prokaryote. In particular, the prokaryote may be selected from the group consisting of the genus *Escherichia* such as *Escherichia coli*; from the genus *Clostridia* such as *Clostridium ljungdahlii*, *Clostridium autoethanogenum*, *Clostridium carboxidivorans* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens*, *Pseudomonas putida* or *Pseudomonas oleavorans*; from the genus *Delftia* such as *Delftia acidovorans*; from the genus *Bacillus* such as *Bacillus subtillis*; from the genus *Lactobacillus* such as *Lactobacillus delbrueckii*; or from the genus *Lactococcus* such as *Lactococcus lactis*.

In another example, hexanoic acid may be produced from synthesis gas by at least one eukaryote. The eukaryote used in the method of the present invention may be selected from the genus *Aspergillus* such as *Aspergillus niger*; from the genus *Saccharomyces* such as *Saccharomyces cerevisiae*; from the genus *Pichia* such as *Pichia pastoris*; from the genus *Yarrowia* such as *Yarrowia lipolytica*; from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*.

More in particular, hexanoic acid may be produced from synthesis gas by any method disclosed in Steinbusch, 2011, Zhang, 2013, Van Eerten-Jansen, M. C. A. A, 2013, Ding H. et al, 2010, Barker H. A., 1949, Stadtman E. R., 1950, Bornstein B. T., et al., 1948 and the like. Even more in particular, the hexanoic acid may be produced from synthesis gas in the presence of at least *Clostridium kluyveri*.

The term "acetogenic bacteria" as used herein refers to a microorganism which is able to perform the Wood-Ljungdahl pathway and thus is able to convert CO, $CO_2$ and/or hydrogen to acetate. These microorganisms include microorganisms which in their wild-type form do not have a Wood-Ljungdahl pathway, but have acquired this trait as a result of genetic modification. Such microorganisms include but are not limited to *E. coli* cells. These microorganisms may be also known as carboxydotrophic bacteria. Currently, 21 different genera of the acetogenic bacteria are known in the art (Drake et al., 2006), and these may also include some *clostridia* (Drake & Kusel, 2005). These bacteria are able to use carbon dioxide or carbon monoxide as a carbon source with hydrogen as an energy source (Wood, 1991). Further, alcohols, aldehydes, carboxylic acids as well as numerous hexoses may also be used as a carbon source (Drake et al., 2004). The reductive pathway that leads to the formation of acetate is referred to as acetyl-CoA or Wood-Ljungdahl pathway. In particular, the acetogenic bacteria may be selected from the group consisting of *Acetoanaerobium notera* (ATCC 35199), *Acetonema longum* (DSM 6540), *Acetobacterium carbinolicum* (DSM 2925), *Acetobacterium malicum* (DSM 4132), *Acetobacterium* species no. 446 (Morinaga et al., 1990, *J. Biotechnol.*, Vol. 14, p. 187-194), *Acetobacterium wieringae* (DSM 1911), *Acetobacterium woodii* (DSM 1030), *Alkalibaculum bacchi* (DSM 22112), *Archaeoglobus fulgidus* (DSM 4304), *Blautia producta* (DSM 2950, formerly *Ruminococcus productus*, formerly *Peptostreptococcus productus*), *Butyribacterium methylotrophicum* (DSM 3468), *Clostridium aceticum* (DSM 1496), *Clostridium autoethanogenum* (DSM 10061, DSM 19630 and DSM 23693), *Clostridium carboxidivorans* (DSM 15243), *Clostridium coskatii* (ATCC no. PTA-10522), *Clostridium drakei* (ATCC BA-623), *Clostridium formicoaceticum* (DSM 92), *Clostridium glycolicum* (DSM 1288), *Clostridium ljungdahlii* (DSM 13528), *Clostridium ljungdahlii* C-01 (ATCC 55988), *Clostridium ljungdahlii* ERI-2

(ATCC 55380), *Clostridium ljungdahlii* O-52 (ATCC 55989), *Clostridium mayombei* (DSM 6539), *Clostridium methoxybenzovorans* (DSM 12182), *Clostridium ragsdalei* (DSM 15248), *Clostridium scatologenes* (DSM 757), *Clostridium* species ATCC 29797 (Schmidt et al., 1986, *Chem. Eng. Commun.*, Vol. 45, p. 61-73), *Desulfotomaculum kuznetsovii* (DSM 6115), *Desulfotomaculum thermobezoicum* subsp. *thermosyntrophicum* (DSM 14055), *Eubacterium limosum* (DSM 20543), *Methanosarcina acetivorans* C2A (DSM 2834), *Moorella* sp. HUC22-1 (Sakai et al., 2004, *Biotechnol. Let.*, Vol. 29, p. 1607-1612), *Moorella thermoacetica* (DSM 521, formerly *Clostridium thermoaceticum*), *Moorella thermoautotrophica* (DSM 1974), *Oxobacter pfennigii* (DSM 322), *Sporomusa aerivorans* (DSM 13326), *Sporomusa ovata* (DSM 2662), *Sporomusa silvacetica* (DSM 10669), *Sporomusa sphaeroides* (DSM 2875), *Sporomusa termitida* (DSM 4440) and *Thermoanaerobacter kivui* (DSM 2030, formerly *Acetogenium kivui*).

More in particular, the strain ATCC BAA-624 of *Clostridium carboxidivorans* may be used. Even more in particular, the bacterial strain labelled "P7" and "P11" of *Clostridium carboxidivorans* as described for example in U.S. 2007/0275447 and U.S. 2008/0057554 may be used.

Another particularly suitable bacterium may be *Clostridium ljungdahlii*. In particular, strains selected from the group consisting of *Clostridium ljungdahlii* PETC, *Clostridium ljungdahlii* ERI2, *Clostridium ljungdahlii* COL and *Clostridium ljungdahlii* O-52 may be used in the conversion of synthesis gas to hexanoic acid. These strains for example are described in WO 98/00558, WO 00/68407, ATCC 49587, ATCC 55988 and ATCC 55989.

The acetogenic bacteria may be used in conjunction with a hydrogen oxidising bacteria. In one example, both an acetogenic bacteria and a hydrogen oxidising bacteria may be used to produce hexanoic acid from synthesis gas. In another example, only acetogenic bacteria may be used for metabolising synthesis gas to produce hexanoic acid from synthesis gas. In yet another example, only a hydrogen oxidising bacteria may be used in this reaction.

The hydrogen oxidising bacteria may be selected from the group consisting of *Achromobacter, Acidithiobacillus, Acidovorax, Alcaligenes, Anabena, Aquifex, Arthrobacter, Azospirillum, Bacillus, Bradyrhizobium, Cupriavidus, Derxia, Helicobacter, Herbaspirillum, Hydrogenobacter, Hydrogenobaculum, Hydrogenophaga, Hydrogenophilus, Hydrogenothermus, Hydrogenovibrio, Ideonella* sp. O1, *Kyrpidia, Metallosphaera, Methanobrevibacter, Myobacterium, Nocardia, Oligotropha, Paracoccus, Pelomonas, Polaromonas, Pseudomonas, Pseudonocardia, Rhizobium,*

*Rhodococcus, Rhodopseudomonas, Rhodospirillum, Streptomyces, Thiocapsa, Treponema, Variovorax, Xanthobacter* and *Wautersia*.

In the production of hexanoic acid from synthesis gas a combination of bacteria may be used. There may be more than one acetogenic bacteria present in combination with one or more hydrogen oxidising bacteria. In another example, there may be more than one type of acetogenic bacteria present only. In yet another example, there may more than one hydrogen oxidising bacteria present only. Hexanoic acid also known as caproic acid has general formula $C_5H_{11}COOH$.

The method according to any aspect of the present invention may further comprise the step of esterification of the hexanoic acid of step A to produce a $C_1$-$C_4$ hexanoate and the $C_1$-$C_4$ hexanoate is contacted with the genetically modified cell of step B. In particular, the method of esterification involves contacting the hexanoic acid of step A with at least one $C_1$-$C_4$ alcohol to produce $C_1$-$C_4$ hexanoate.

In another example, the production of hexanoic acid from synthesis gas may involve the use of the acetogenic bacteria in conjunction with a bacterium capable of producing the hexanoic acid using ethanol-carboxylate fermentation hydrogen oxidising bacteria. In one example, both an acetogenic bacteria and a hydrogen oxidising bacteria may be used to produce hexanoic acid from synthesis gas. For example, *Clostridium ljungdahlii* may be used simultaneously with *Clostridium kluyveri*. In another example, only acetogenic bacteria may be used for metabolising synthesis gas to produce hexanoic acid from synthesis gas. In this example, the acetogenic bacteria may be capable of carrying out both the ethanol-carboxylate fermentation pathway and the Wood-Ljungdahl pathway. In one example, the acetogenic bacteria may be *C. carboxidivorans* which may be capable of carrying out both the Wood-Ljungdahl pathway and the ethanol-carboxylate fermentation pathway.

The ethanol-carboxylate fermentation pathway is described in detail at least in Seedorf, H., et al., 2008. The organism may be selected from the group consisting of *Clostridium kluyveri, C. Carboxidivorans* and the like. These microorganisms include microorganisms which in their wild-type form do not have an ethanol-carboxylate fermentation pathway, but have acquired this trait as a result of genetic modification. In particular, the microorganism may be *Clostridium kluyveri*.

In one example, the cell carrying out step A according to any aspect of the present invention may be a genetically modified microorganism. The genetically modified cell or microorganism may be genetically different from the wild type cell or microorganism. The genetic difference between the genetically modified microorganism according to any aspect of the present invention and the wild type microorganism may be in the presence of a complete gene, amino acid, nucleotide etc. in the genetically modified microorganism that may be absent in the wild type microorganism. In one example, the genetically modified microorganism according to any aspect of the present invention may comprise enzymes that enable the microorganism to produce hexanoic acid. The wild type microorganism relative to the genetically modified microorganism of the present invention may have none or no detectable activity of the enzymes that enable the genetically modified microorganism to produce the hexanoic acid. As used herein, the term 'genetically modified microorganism' may be used interchangeably with the term 'genetically modified cell'. The genetic modification according to any aspect of the present invention is carried out on the cell of the microorganism.

In one example, the microorganism may be a wild type organism that expresses at least one enzyme selected $E_1$ to $E_{10}$, wherein $E_1$ is an alcohol dehydrogenase (adh), $E_2$ is an acetaldehyde dehydrogenase (aid), $E_3$ is an acetoacetyl-CoA thiolase (thl), $E_4$ is a 3-hydroxybutyryl-CoA dehydrogenase (hbd), $E_5$ is a 3-hydroxybutyryl-CoA dehydratase (crt), $E_6$ is a butyryl-CoA dehydrogenase (bcd), $E_7$ is an electron transfer flavoprotein subunit (etf), $E_8$ is a coenzyme A transferase (cat), $E_9$ is an acetate kinase (ack) and $E_{10}$ is phosphotransacetylase (pta). In particular, the wild type microorganism according to any aspect of the present invention may express at least $E_2$, $E_3$ and $E_4$. Even more in particular, the wild type microorganism according to any aspect of the present invention may express at least $E_4$.

In another example, the microorganism according to any aspect of the present invention may be a genetically modified organism that has increased expression relative to the wild type microorganism of at least one enzyme selected $E_1$ to $E_{10}$, wherein $E_1$ is an alcohol dehydrogenase (adh), $E_2$ is an acetaldehyde dehydrogenase (aid), $E_3$ is an acetoacetyl-CoA thiolase (thl), $E_4$ is a 3-hydroxybutyryl-CoA dehydrogenase (hbd), $E_5$ is a 3-hydroxybutyryl-CoA dehydratase (crt), $E_6$ is a butyryl-CoA dehydrogenase (bcd), $E_7$ is an electron transfer flavoprotein subunit (etf), $E_8$ is a coenzyme A transferase (cat), $E_9$ is an acetate kinase (ack) and $E_{10}$ is phosphotransacetylase (pta). In particular, the genetically modified microorganism according to any aspect of the present invention may express at least enzymes $E_2$, $E_3$ and $E_4$. Even more in particular, the genetically modified microorganism according to any aspect of the present invention may express at least $E_4$. The enzymes $E_1$ to $E_{10}$ may be isolated from *Clostridium kluyveri*.

According to any aspect of the present invention, $E_1$ may be an ethanol dehydrogenase. In particular, $E_1$ may be selected from the group consisting of alcohol dehydrogenase 1, alcohol dehydrogenase 2, alcohol dehydrogenase 3, alcohol dehydrogenase B and combinations thereof. More in particular, $E_1$ may comprise sequence identity of at least 50% to a polypeptide selected from the group consisting of CKL_1075, CKL_1077, CKL_1078, CKL_1067, CKL_2967, CKL_2978, CKL_3000, CKL_3425, and CKL_2065. Even more in particular, $E_1$ may comprise a polypeptide with sequence identity of at least 50, 60, 65, 70, 75, 80, 85, 90, 91, 94, 95, 98 or 100% to a polypeptide selected from the group consisting of CKL_1075, CKL_1077, CKL_1078 and CKL_1067.

According to any aspect of the present invention, $E_2$ may be an acetaldehyde dehydrogenase. In particular, $E_2$ may be selected from the group consisting of acetaldehyde dehydrogenase 1, alcohol dehydrogenase 2 and combinations thereof. In particular, $E_2$ may comprise sequence identity of at least 50% to a polypeptide selected from the group consisting of CKL_1074, CKL_1076 and the like. More in particular, $E_2$ may comprise a polypeptide with sequence identity of at least 50, 60, 65, 70, 75, 80, 85, 90, 91, 94, 95, 98 or 100% to a polypeptide selected from the group consisting of CKL_1074 and CKL_1076.

According to any aspect of the present invention, $E_3$ may be selected from the group consisting of acetoacetyl-CoA thiolase A1, acetoacetyl-CoA thiolase A2, acetoacetyl-CoA thiolase A3 and combinations thereof. In particular, $E_3$ may comprise sequence identity of at least 50% to a polypeptide selected from the group consisting of CKL_3696, CKL_3697, CKL_3698 and the like. More in particular, $E_3$ may comprise a polypeptide with sequence identity of at least 50, 60, 65, 70, 75, 80, 85, 90, 91, 94, 95, 98 or 100% to a polypeptide selected from the group consisting of CKL_3696, CKL_3697 and CKL_3698.

According to any aspect of the present invention, $E_4$ may be 3-hydroxybutyryl-CoA dehydrogenase 1, 3-hydroxybutyryl-CoA dehydrogenase 2 and the like. In particular, $E_4$ may comprise sequence identity of at least 50% to a polypeptide CKL_0458, CKL_2795 and the like. More in particular, $E_4$ may comprise a polypeptide with sequence identity of at least 50, 60, 65, 70, 75, 80, 85, 90, 91, 94, 95, 98 or 100% to the polypeptide CKL_0458 or CKL_2795.

According to any aspect of the present invention, $E_5$ may be 3-hydroxybutyryl-CoA dehydratase 1, 3-hydroxybutyryl-CoA dehydratase 2 and combinations thereof. In particular, $E_5$ may comprise sequence identity of at least 50% to a polypeptide selected from the group consisting of CKL_0454, CKL_2527 and the like. More in particular, $E_5$ may comprise a polypeptide with sequence identity of at least 50, 60, 65, 70, 75, 80, 85, 90, 91, 94, 95, 98 or 100% to a polypeptide selected from the group consisting of CKL_0454 and CKL_2527.

According to any aspect of the present invention, $E_6$ may be selected from the group consisting of butyryl-CoA dehydrogenase 1, butyryl-CoA dehydrogenase 2 and the like. In particular, $E_6$ may comprise sequence identity of at least 50% to a polypeptide selected from the group consisting of CKL_0455, CKL_0633 and the like. More in particular, $E_6$ may comprise a polypeptide with sequence identity of at least 50, 60, 65, 70, 75, 80, 85, 90, 91, 94, 95, 98 or 100% to a polypeptide selected from the group consisting of CKL_0455 and CKL_0633.

According to any aspect of the present invention, $E_7$ may be selected from the group consisting of electron transfer flavoprotein alpha subunit 1, electron transfer flavoprotein alpha subunit 2, electron transfer flavoprotein beta subunit 1 and electron transfer flavoprotein beta subunit 2. In particular, $E_7$ may comprise sequence identity of at least 50% to a polypeptide selected from the group consisting of CKL_3516, CKL_3517, CKL_0456, CKL_0457 and the like. More in particular, $E_7$ may comprise a polypeptide with sequence identity of at least 50, 60, 65, 70, 75, 80, 85, 90, 91, 94, 95, 98 or 100% to a polypeptide selected from the group consisting of CKL_3516, CKL_3517, CKL_0456 and CKL_0457.

According to any aspect of the present invention, $E_8$ may be coenzyme transferase (cat). In particular, $E_8$ may be selected from the group consisting of butyryl-CoA: acetate CoA transferase, succinyl-CoA:coenzyme A transferase, 4-hydroxybutyryl-CoA: coenzyme A transferase and the like. More in particular, $E_8$ may comprise sequence identity of at least 50% to a polypeptide selected from the group consisting of CKL_3595, CKL_3016, CKL_3018 and the like. More in particular, $E_8$ may comprise a polypeptide with sequence identity of at least 50, 60, 65, 70, 75, 80, 85, 90, 91, 94, 95, 98 or 100% to a polypeptide selected from the group consisting of CKL_3595, CKL_3016 and CKL_3018.

According to any aspect of the present invention, $E_9$ may be an acetate kinase A (ack A). In particular, $E_9$ may comprise sequence identity of at least 50% to a polypeptide sequence of CKL_1391 and the like. More in particular, $E_9$ may comprise a polypeptide with sequence identity of at least 50, 60, 65, 70, 75, 80, 85, 90, 91, 94, 95, 98 or 100% to a polypeptide of CKL_1391.

According to any aspect of the present invention, $E_{10}$ may be phosphotransacetylase (pta). In particular, $E_{10}$ may comprise sequence identity of at least 50% to a polypeptide sequence of CKL_1390 and the like. More in particular, $E_{10}$ may comprise a polypeptide with sequence identity of at least 50, 60, 65, 70, 75, 80, 85, 90, 91, 94, 95, 98 or 100% to a polypeptide of CKL_1390.

In one example the microorganism, wild-type or genetically modified expresses $E_1$-$E_{10}$. In particular, the microorganism according to any aspect of the present invention may have increased expression relative to the wild type microorganism of $E_1$, $E_2$, $E_3$, $E_4$, $E_5$, $E_6$, $E_7$, $E_8$, $E_9$, $E_{10}$ or combinations thereof. In one example, the genetically modified microorganism has increased expression relative to the wild type microorganism of $E_1$, $E_2$, $E_3$, $E_4$, $E_5$, $E_6$, $E_7$, $E_8$, $E_9$ and $E_{10}$. More in particular, a combination of any of the enzymes $E_1$-$E_{10}$ may be present in the organism to enable at least one carboxylic acid to be produced. In one example, the genetically modified organism used according to any aspect of the present invention may comprise a combination of any of the enzymes $E_1$-$E_{10}$ that enable the organism to produce at least one, or two or three types of carboxylic acids at the same time. For example, the microorganism may be able to produce hexanoic acid, butyric acid and/or acetic acid at the simultaneously. Similarly, the microorganism may be genetically modified to express a combination of enzymes $E_1$-$E_{10}$ that enable the organism to produce either a single type of carboxylic acid or a variety of carboxylic acids. In all the above cases, the microorganism may be in its wild-type form or be genetically modified.

In one example, the genetically modified microorganism according to any aspect of the present invention has increased expression relative to the wild type microorganism of hydrogenase maturation protein and/or electron transport complex protein. In particular, the hydrogenase maturation protein (hyd) may be selected from the group consisting of hydE, hydF or hydG. In particular, the hyd may comprise sequence identity of at least 50% to a polypeptide selected from the group consisting of CKL_0605, CKL_2330, CKL_3829 and the like. More in particular, the hyd used according to any aspect of the present invention may comprise a polypeptide with sequence identity of at least 50, 60, 65, 70, 75, 80, 85, 90, 91, 94, 95, 98 or 100% to a polypeptide selected from the group consisting of CKL_0605, CKL_2330 and CKL_3829.

Throughout this application, any data base code, unless specified to the contrary, refers to a sequence available from the NCBI data bases, more specifically the version online on 12 Jun. 2014, and comprises, if such sequence is a nucleotide sequence, the polypeptide sequence obtained by translating the former.

The method according to any aspect of the present invention, may further comprise the step of esterification of the hexanoic acid of step A to produce a $C_1$-$C_4$ hexanoate and the $C_1$-$C_4$ hexanoate is contacted with the genetically modified cell of step B.

In one example, the method of esterification may be a chemical process. Any chemical reaction known in the art may be used to convert hexanoic acid to $C_1$-$C_4$ alcohol hexanoate. More in particular, the method involves reacting hexanoic acid with an alcohol. Hexanoic acid may be contacted with at least one short-chained carbon alcohol to produce a hexanoate. In particular, the short-chained carbon alcohol may be a $C_1$-$C_4$ alcohol. The short chain alcohol may be methanol, ethanol, isopropyl alcohol, and/or butyl alcohol. In particular, the alcohol may be selected from the group consisting of methanol, ethanol, isopropyl alcohol, and/or butyl alcohol to produce methyl, ethyl, propyl or butyl hexanoate respectively. This reaction may take place in the presence of at least one catalyst. The catalyst is usually an acidic catalyst such as s sulphonic acid, a base such as an alkali hydroxide or an alkali alcoholate, a metal oxide or a metal alkylate. In particular, hexanoic acid may be metabolised to form C1-C4 alcohol hexanoate. In particular, the catalyst may be $ZrOCl_2.8H_2O$.

In one example, the hexanoic acid reacts with methanol in the presence of $ZrOCl_2.8H_2O$ to produce methyl hexanoate.

The method according to any aspect of the present invention may comprise a step of extracting the hexanoic acid produced from the synthesis gas first before contacting the hexanoic acid with at least one $C_1$-$C_4$ alcohol. Any method known in the art for extracting hexanoic acid may be used. In particular, one example of an extraction method of hexanoic acid is provided in section 2.3 of Byoung, S. J et al. 2013. Another example may the method disclosed under the section 'Extraction Model' in Kieun C., Et al., 2013.

In another example, the method of esterification may be a biochemical process where at least one enzyme may be involved in catalysing the esterification process. The enzyme for esterification may be selected from the group consisting of a thioesterase enzyme, an acyl-CoA synthetase enzyme, an ester synthase enzyme and a lipase. At least one of these enzymes may be expressed in the bacteria of step A of the method of the present invention. In one example, the acetogenic bacteria and/or hydrogen oxidising bacteria may overexpress an esterification enzyme that may be capable of esterification of the hexanoic acid. In another example, a further cell expressing an esterification enzyme may be included after step A of the method of the present invention to esterify the hexanoic acid to a hexanoate.

The hexanoic acid from step A of the method of the present invention may be directly converted to aminohexanoic acid and/or aminohexanoic acid ester. In another example, the hexanoic acid from step A of the method of the present invention may first be esterified to a hexanoate either chemically or biochemically. This hexanoate is then contacted with the genetically modified cell of step B of the method of the present invention. In one example, both a chemical and biochemical process is carried out in combination sequentially or simultaneously to esterify the hexanoic acid.

The $C_1$-$C_4$ alcohol hexanoate may then be contacted with a genetically modified cell to produce an aminohexanoic acid and/or aminohexanoic acid ester, wherein the genetically modified cell has an increased activity, in comparison with its wild type, of at least one enzyme selected from the group consisting of alkane monooxygenase, alcohol dehydrogenase, and ω-transaminase.

The cell according to any aspect of the present invention has been genetically modified relative to its wild type so that, in comparison with its wild type, it is able to produce more aminohexanoic acids and/or aminohexanoic acid esters, starting from $C_1$ to $C_4$ alcohol hexanoate. Such a cell may be used to produce aminohexanoic acids and/or aminohexanoic acid esters from aminohexanoic acids by fermentation from $C_1$ to $C_4$ alcohol hexanoate.

The phrase "that in comparison with its wild type it is able to produce more aminohexanoic acids and/or aminohexanoic acid esters, starting from methyl hexanoate" also applies to the case when the wild type of the genetically modified cell is not able to form any aminohexanoic acid, and/or aminohexanoic acid ester to begin with. Also included are wild type cells that produce at least no detectable amounts of these compounds and it is only after the genetic modification of the wild type to produce the cell used in any method of the present invention are there detectable amounts of these compounds formed.

The phrase "wild type" as used herein in conjunction with a cell may denote a cell with a genome make-up that is in a form as seen naturally in the wild. The term may be applicable for both the whole cell and for individual genes. The term "wild type" therefore does not include such cells or such genes where the gene sequences have been altered at least partially by man using recombinant methods.

In particular, the genetically modified cell may have been genetically modified so that in a defined time interval, for example within 2 hours, particularly within 8 hours and more particularly within 24 hours, it forms at least twice, in particular at least 10 times, more in particular at least 100, 1000 or 10000 times more aminohexanoic acids and/or aminohexanoic acid esters than the wild-type cell. The increase in product formation can be determined for example by cultivating the cell used according to the method of the invention and the wild-type cell each separately under the same conditions (same cell density, same nutrient medium, same culture conditions) for a specified time interval in a suitable nutrient medium and then determining the amount of target product (aminohexanoic acids and/or aminohexanoic acid esters) in the nutrient medium.

The cells used according to the method of the invention can be prokaryotes or eukaryotes. They can be mammalian cells (such as human cells or non-human cells), plant cells or microorganisms such as yeasts, fungi or bacteria. In particular, the microorganisms may be bacteria. More in particular, the microorganism may be yeasts.

Suitable bacteria, yeasts or fungi may be those bacteria, yeasts or fungi that have been deposited in the German Collection of Microorganisms and Cell Cultures (Deutsche Sammlung von Mikroorganismen and Zellkulturen GmbH, abbreviated to DSMZ), Brunswick, Germany, as strains of bacteria, yeasts or fungi. Suitable bacteria that may be used in the method of the invention may belong to the genera listed at www.dsmz.de/species/bacteria.htm. Suitable yeasts that may be used in the method of the invention belong to the genera listed at www.dsmz.de/species/yeasts.htm Suitable fungi that may be used in the method of the invention may belong to the genera listed at www.dsmz.de/species/fungi.htm.

In particular, the cells that may be genetically modified and used in the method of the present invention may be selected from the genera *Corynebacterium, Brevibacterium, Bacillus, Lactobacillus, Lactococcus, Candida, Pichia, Kluveromyces, Saccharomyces, Escherichia, Zymomonas, Yarrowia, Methylobacterium, Ralstonia, Pseudomonas, Burkholderia* and *Clostridium*. More in particular, the cells that may be used in the method of the present invention may be selected from the group consisting of *Escherichia coli, Corynebacterium glutamicum* and *Pseudomonas putida*. Even more in particular, the cells that may be used in the method of the present invention may be *Escherichia coli*. The *E. coli* may be of any strain known in the art. In particular, the strain may be JM101.

In particular, in comparison with its wild type, increased activity of at least one of the following enzymes may be found in the genetically modified cell according to the method of the present invention:
  i) an alkane monooxygenase which catalyses the conversion of carboxylic acids or carboxylic acid esters to the corresponding ω-hydroxycarboxylic acids and/or ω-hydroxycarboxylic acid esters;
  ii) an alcohol dehydrogenase which catalyses the conversion of ω-hydroxycarboxylic acids and/or ω-hydroxycarboxylic acid esters to the corresponding ω-oxocarboxylic acids or (ω-oxocarboxylic acid esters; and/or
  iii) ω-transaminase which catalyses the conversion of ω-oxocarboxylic acids or ω-oxocarboxylic acid esters to the corresponding ω-aminocarboxylic acids or ω-aminocarboxylic acid esters.

The phrase "increased activity of an enzyme", as used herein is to be understood as increased intracellular activity. Basically, an increase in enzymatic activity can be achieved by increasing the copy number of the gene sequence or gene sequences that code for the enzyme, using a strong promoter or employing a gene or allele that codes for a corresponding enzyme with increased activity and optionally by combining these measures. Genetically modified cells used in the method according to the invention are for example produced by transformation, transduction, conjugation or a combination of these methods with a vector that contains the desired gene, an allele of this gene or parts thereof and a vector that makes expression of the gene possible. Heterologous expression is in particular achieved by integration of the gene or of the alleles in the chromosome of the cell or an extrachromosomally replicating vector.

The cells according to any aspect of the present invention are genetically transformed according to any method known in the art. In particular, the cells may be produced according to the method disclosed in WO/2009/077461.

The phrase 'the genetically modified cell has an increased activity, in comparison with its wild type, in enzymes' as used herein refers to the activity of the respective enzyme that is increased by a factor of at least 2, in particular of at least 10, more in particular of at least 100, yet more in particular of at least 1000 and even more in particular of at least 10000.

According to any aspect of the present invention, the cell may have increase in activity of alkane monohydrogenase, alcohol dehydrogenase or ω-transaminase only or combinations thereof. In particular, the increase in activity may be in alkane monohydrogenase and alcohol dehydrogenase or alkane monohydrogenase, and ω-transaminase or alcohol dehydrogenase and ω-transaminase. In particular, the cell may have increase in activity of alkane monohydrogenase, alcohol dehydrogenase and ω-transaminase.

The enzyme alkane monooxygenase may be encoded by the AlkBGT gene from *Pseudomonas putida* GPO1. The isolation of the AlkBGT gene sequence is described for example in van Beilen et al., 2002. Furthermore, cytochrome P450 monoxygenases, in particular cytochrome P450 monoxygenases from *Candida*, for example from *Candida tropicalis*, or from plants, for example from the chick-pea (*Cicer arietinum* L.), can also be used as alkane monoxygenases. The gene sequences of suitable cytochrome P450 monoxygenases from *Candida tropicalis* are for example disclosed in WO00/20566, whereas the gene sequences of suitable cytochrome P450 monoxygenases from the chick-pea are given for example in Barz et al., 2000. Other homologues of the AlkB gene are also given in van Beilen et al., 2003. A suitable gene for a xylene monooxygenase is for example the xylM or the xylA gene, and a plasmid containing these two genes has the GENBANK Accession No. M37480. In particular, the gene sequence encoding alkane monoxygenase may be from *Pseudomonas oleovorans* and may comprise or may be the sequence of SEQ ID NO. 1 (Table 1).

The enzyme alcohol dehydrogenase may be encoded by the AlkJ gene (EC 1.1.99-2) from *Pseudomonas putida* GPO1, *Alcanivorax borkumensis*, *Bordetella parapertussis*, *Bordetella bronchiseptica* and *Roseobacter denitrificans*. In particular, the AlkJ gene may be encoded by *Pseudomonas oleovorans*. The gene sequences for the alcohol dehydrogenases encoded by the AlkJ gene can be found for example in the KEGG gene databank. In particular, the gene sequence encoding AlkJ gene may comprise or may be SEQ ID NO:2 (Table 1).

The enzyme ω-transaminase may be selected from the ω-transaminases that are characterized in US-A-2007/0092957 by the sequence numbers 248, 250, 252 and 254.

In another example, the ω-transaminases may be isolated from plants. The ω-transaminases from plants may be selected from the group consisting of *Arabidopsis thaliana*, *Avena sativa*, *Beta vulgaris*, *Glycine max*, *Hordeum vulgare*, *Lotus japonicus*, *Solanum lycopersicum*, *Manihot esculenta*, *Oryza sativa*, *Traeticum aestivum*, *Zea mays*, *Spinacia oleracea*, *Arum maculatum*, *Mercurialis perennis* and *Urtica dioica*.

In particular, the ω-transaminase CV2025 from *Chromobacterium violaceum* DSM30191 may be used in the recombinant cell for the method of the present invention. More in particular, the ω-transaminase is the ω-transaminase from *Chromobacterium violaceum* DSM30191 (Kaulmann et al., 2007), which is encoded by the gene sequence according to SEQ ID NO:3 (Table 1).

TABLE 1

Nucleotide sequences of the genes used to genetically modify the cell according to any aspect of the present invention.

| SEQ ID NO: | nucleotide sequence |
|---|---|
| 1 | CTTGAGAAACACAGAGTTCTGGATTCCGCTCCAGAGTACGTAGATAAAAAGAAATATCTC<br>TGGATACTATCAACTTTGTGGCCGGCTACTCCGATGATCGGAATCTGGCTTGCAAATGAA<br>ACTGGTTGGGGGATTTTTTATGGGCTGGTATTGCTCGTATGGTACGGCGCACTTCCATTG<br>CTTGATGCGATGTTTGGTGAGGACTTTAATAATCCGCCTGAAGAAGTGGTGCCGAAACTA<br>GAGAAGGAGCGGTACTATCGAGTTTTGACATATCTAACAGTTCCTATGCATTACGCTGCA<br>TTAATTGTGTCAGCATGGTGGGTCGGAACTCAGCCAATGTCTTGGCTTGAAATTGGTGCG<br>CTTGCCTTGTCACTGGGTATCGTGAACGGACTAGCGCTCAATACAGGACACGAACTCGGT<br>CACAAGAAGGAGACTTTTGATCGTTGGATGGCCAAAATTGTGTTGGCTGTCGTAGGGTAC<br>GGTCACTTCTTTATTGAGCATAATAAGGGTCATCACCGTGATGTCGCTACACCGATGGAT<br>CCTGCAACATCCCGGATGGGAGAAAGCATTTATAAGTTTTCAATCCGTGAGATCCCAGGA<br>GCATTTATTCGTCTTGGGGGCTTGAGGAACAACGCCTTTCGCGCCGTGGCCAAAGCGTT<br>TGGAGTTTCGATAATGAAATCCTCCAACCAATGATCATCACAGTTATTCTTTACGCCGTT<br>CTCCTTGCCTTGTTTGGACCTAAGATGCTGGTGTTCCTGCCGATTCAAATGGCTTTCGGT<br>TGGTGGCAGCTGACCAGTGCGAACTATATTGAACATTACGGCTTGCTCCGTCAAAAAATG<br>GAGGACGGTCGATATGAGCATCAAAAGCCGCACCATTCTTGGAATAGTAATCACATCGTC<br>TCTAATCTAGTGCTGTTCCACCTTCAGCGGCACTCGGATCACCACGCGCATCCAACACGT<br>TCTTATCAGTCACTTCGGGATTTTCCCGGCCTGCCGGCTCTTCCGACGGGTTACCCTGGT<br>GCATTTTTGATGGCGATGATTCCTCAGTGGTTTAGATCAGTTATGGATCCCAAGGTAGTA |

TABLE 1-continued

Nucleotide sequences of the genes used to
genetically modify the cell according to any
aspect of the present invention.

| SEQ ID NO: | nucleotide sequence |
|---|---|
| | GATTGGGCTGGTGGTGACCTTAATAAGATCCAAATTGATGATTCGATGCGAGAAACCTAT<br>TTGAAAAAATTTGGCACTAGTAGTGCTGGTCATAGTTCGAGTACCTCTGCGGTAGCATCG<br>TAG |
| 2 | ATGTACGACTATATAATCGTTGGTGCTGGATCTGCAGGATGTGTGCTTGCTAATCGTCTT<br>TCGGCCGACCCCTCTAAAAGAGTTTGTTTACTTGAAGCTGGGCCGCGAGATACGAATCCG<br>CTAATTCATATGCCGTTAGGTATTGCTTTGCTTTCAAATAGTAAAAAGTTGAATTGGGCT<br>TTTCAAACTGCGCCACAGCAAAATCTCAACGGCCGGAGCCTTTTCTGGCCACGAGGAAAA<br>ACGTTAGGTGGTTCAAGCTCAATAACGCAATGGTCTATATCCGAGGGCATGAAGACGAT<br>TACCACGCATGGGAGCAGGCGGCCGGCCGCTACTGGGGTTGGTACCGGGCTCTTGAGTTG<br>TTCAAAAGGCTTGAATGCAACCAGCGATTCGATAAGTCCGAGCACCATGGGGTTGACGGA<br>GAATTAGCTGTTAGTGATTTAAAATATATCAATCCGCTTAGCAAAGCATTCGTGCAAGCC<br>GGCATGGAGGCCAATATTAATTTCAACGGAGATTTCAACGGCGAGTACCAGGACGGCGTA<br>GGGTTCTATCAAGTAACCCAAAAAAATGGACAACGCTGGAGCTCGGCGCGTGCATTCTTG<br>CACGGTGTACTTTCCAGACCAAATCTAGACATCATTACTGATGCGCATGCATCAAAAATT<br>CTTTTTGAAGACCGTAAGGCGGTTGGTGTTTCTTATATAAAGAAAAATATGCACCATCAA<br>GTCAAGACAACGAGTGGTGGTGAAGTACTTCTTAGTCTTGGCGCAGTCGGCACGCCTCAC<br>CTTCTAATGCTTTCTGGTGTTGGGGCTGCAGCCGAGCTTAAGGAACATGGTGTTTCTCTA<br>GTCCATGATCTTCCTGAGGTGGGGAAAAATCTTCAAGATCATTTGGACATCACATTGATG<br>TGCGCAGCAAATTCGAGAGAGCCGATAGGTGTTGCTCTTCTTTCATCCCTCGTGGTGTC<br>TCGGGTTTGTTTTCATATGTGTTTAAGCGCGAGGGGTTTCTCACTAGTAACGTGGCAGAG<br>TCGGGTGGTTTTGTAAAAAGTTCTCCTGATCGTGATCGGCCCAATTTGCAGTTTCATTTC<br>CTTCCAACTTATCTTAAAGATCACGGTCGAAAAATAGCGGGTGGTTATGGTTATACGCTA<br>CATATATGTGATCTTTTGCCTAAGAGCCGAGGCAGAATTGGCCTAAAAAGCGCCAATCCA<br>TTACAGCCGCCTTTAATTGACCCGAACTATCTTAGCGATCATGAAGATATTAAAACCATG<br>ATTGCGGGTATTAAGATAGGGCGCGCTATTTTGCAGGCCCCATCGATGGCGAAGCATTTT<br>AAGCATGAAGTAGTACCGGGCCAGGCTGTTAAAACTGATGATGAAATAATCGAAGATATT<br>CGTAGGCGAGCTGAGACTATATACCATCCGGTAGGTACTTGTAGGATGGGTAAAGATCCA<br>GCGTCAGTTGTTGATCCGTGCCTGAAGATCCGTGGGTTGGCAAATATTAGAGTCGTTGAT<br>GCGTCAATTATGCCGCACTTGGTCGCGGGTAACACAAACGCTCCAACTATTATGATTGCA<br>GAAAATGCGGCAGAAATAATTATGCGGAATCTTGATGTGGAAGCATTAGAGGCTAGCGCT<br>GAGTTTGCTCGCGAGGGTGCAGAGCTAGAGTTGGCA |
| 3 | ATGCAGAAACAGCGTACCACCTCTCAGTGGCGTGAACTCGATGCGGCGCATCATCTCCAT<br>CCGTTTACCGATACCGCGAGCCTCAATCAGGCGGGTGCGCGTGTGATGACCCGTGGCGAA<br>GGCGTGTATCTCTGGGATAGCGAAGGCAACAAAATTATTGATGGCATGGCGGGCCTCTGG<br>TGCGTGAACGTGGCTATGGCCGTAAAGATTTTGCGGAAGCGGCGCGTCGTCAGATGGAA<br>GAACTCCCGTTTTATAACACCTTCTTTAAAACCACCCATCCGGCGGTGGTGGAACTCAGC<br>AGCCTCCTCGCCGAAGTTACCCCGGCAGGTTTTGATCGTGTGTTTTATACCAACAGCGGC<br>AGCGAAAGCGTGGATACCATGATTCGTATGGTGCGTCGTTATTGGGATGTGCAGGGCAAA<br>CCGGAAAAAAAAACCCTCATTGGCCGTTGGAACGGCTATCACGGCAGCACCATTGGCGGT<br>GCGAGCCTCGGCGGCATGAAATATATGCATGAACAGGGCGATCTCCCGATTCCGGGCATG<br>GCGCATATTGAACAGCCGTGGTGGTATAAACATGGCAAAGATATGACCCCGGATGAATTT<br>GGCGTGGTTGCGGCGCGTTGGCTCGAAGAAAAAATTCTCGAAATCGGCGCGGATAAAGTG<br>GCGGCGTTTGTGGGCGAACCGATTCAGGGTGCGGGCGGTGTGATTGTTCCGCCGGCAACC<br>TATTGGCCGGAAATTGAACGTATTTGCCGCAAATATGATGTGCTCCTCGTTGCGGATGAA<br>GTGATTTGCGGCTTTGGCCGTACCGGCGAATGGTTTGGCCATCAGCATTTTGGCTTTCAG<br>CCGGACCTCTTTACCGCGGCGAAAGGCCTCAGCAGCGGCTATCTCCCGATTGGCGCGGTG<br>TTTGTGGGCAAACGTGTTGCGGAAGGTCTCATTGCGGGCGGTGATTTTAACCATGGCTTT<br>ACCTATAGCGGCCATCCGGTGTGTGCGGCGGTGGCGCATGCGAATGTTGCGGCGCTCCGT<br>GATGAAGGCATTGTGCAGCGTGTGAAAGATGATATTGGCCCGTATATGCAGAAACGTTGG<br>CGTGAAACCTTTAGCCGTTTTGAACATGTGGATGATGTGCGTGGCGTGGGCATGGTGCAG<br>GCGTTTACCCTCGTGAAAAACAAAGCGAAACGTGAACTCTTTCCGGATTTTGGCGAAATT<br>GGCACCCTCTGCCGCGATATTTTTTTTCGCAACAACCTCATTATGCGTGCGTGCGGCGAT<br>CACATTGTGTCTGCACCGCCGCTCGTTATGACCCGTGCGGAAGTGGATGAAATGCTCGCC<br>GTGGCGGAACGTTGCCTCGAAGAATTTGAACAGACCCTCAAAGCGCGTGGCCTCGCCTAA |
| 4 | ATGGCAATCGTTGTTGTTGGCGCTGGTACAGCTGGAGTAAATGCTGCGTTCTGGCTTCGT<br>CAATATGGTTATAAAGGGGAAATTAGGATTTTTAGCAGGGAGTCTGTGGCGCCTTATCAG<br>CGGCCTCCTCTATCCAAGGCTTTTCTGACAAGTGAGATTGCAGAATCCGCAGTGCCATTA<br>AAGCCAGAAGGTTTTTATACGAATAACAATATTACCATTTCGTTAAATACACCGATTGTA<br>TCAATCGACGTGGGCGTAAGATAGTTTCTTCTAAAGATGGAAAAGAATACGCGTATGAA<br>AAATTGATTCTTGCAACACCTGCTAGCGCACGTAGGTTAACCTGCGAGGGGTCTGAACTG<br>TCTGGGGTCTGCTATTTACGCAGTATGGAAGACGCCAAAAATTTACGTAGGAAACTTGTG<br>GAGAGTGCGTCTGTTGTTGTTGGGCGGCGGAGTAATCGGGCTTGAAGTCGCCTCAGCT<br>GCGGTGGGCTTAGGGAAGAGGGTCACAGTGATAGAGCCACCCCGCGTGTAATGGCGCGC<br>GTGGTTACGCCGGCAGCAGCAAACTTAGTCAGAGCCCGCCTGGAGGCTGAAGGAATTGAG<br>TTCAAGCTGAATGCGAAATTAACGTCTATAAAGGGCAGGAATGGCCATGTTGAACAATGC<br>GTACTTGAAAGTGGAGAAGAAATTCAGGCGGATCTGATTGTAGTTGGAATCGGTGCTATC<br>CCAGAGCTAGAGCTGGCAACTGAGGCGGCCCTTGAAGTGAGTAATGGTGTTGTGGTCGAT<br>GATCAGATGTGTACATCGGATACAAGTATATATGCAATCGGCGACTGCGCAATGGCTAGA<br>AATCCTTTTTGGGGAACGATGGTACGTTTAGAGACAATTCATAATGCGGTTACACACGCT<br>CAAATTGTCGCAAGTAGCATCTGTGGCACATCAACACCAGCACCAACCCCACCACGGTTC |

TABLE 1-continued

Nucleotide sequences of the genes used to genetically modify the cell according to any aspect of the present invention.

| SEQ ID NO: | nucleotide sequence |
|---|---|
|  | TGGTCTGATCTTAAAGGGATGGCGCTGCAAGGACTTGGTGCTCTAAAGGACTACGATAAA<br>CTCGTTGTTGCAATTAATAACGAAACTCTTGAACTAGAAGTCCTTGCGTACAAGCAGGAG<br>CGACTGATTGCAACTGAGACAATAAATTTGCCTAAACGTCAAGGTGCGCTTGCAGGGAGT<br>ATAAAATTACCTGATTAG |
| 9 | ATGGCTAGCTATAAATGCCCGGATTGTAATTATGTTTATGATGAGAGTGCGGGTAATGTG<br>CATGAGGGGTTTTCTCCAGGTACGCCTTGGCACCTTATTCCTGAGGATTGGTGCTGCCCC<br>GATTGCGCCGTTCGAGACAAGCTTGACTTCATGTTAATTGAGAGCGGCGTAGGTGAAAAG<br>GGCGTCACCTCAACCCATACTTCGCCAAATTTATCCGAGGTTAGTGGCACAAGTTTAACT<br>GCTGAAGCAGTGGTTGCGCCGACAAGCTTAGAGAAATTGCCTAGTGCCGACGTTAAAGGC<br>CAAGATCTATATAAAACTCAACCTCCAAGGTCTGATGCCCAAGGCGGGAAAGCATACTTG<br>AAGTGGATATGTATTACTTGTGGCCATATATATGATGAGGCGTTGGGCGATGAGGCCGAG<br>GGTTTTACTCCAGGTACTCGCTTTGAGGATATTCCTGATGACTGGTGCTGTCCGGATTGC<br>GGGGCTACGAAAGAAGACTATGTGCTCTACGAGGAAAAG |

Enzymes that are encoded by nucleic acids that have 90%, 95%, 99% and in particular 100% identity to the sequences according to SEQ ID NOs: 1, 2 and 3, are suitable in the method of the present invention. The "nucleotide identity" relative to SEQ ID NOs:1-3 is determined using known methods. In general, special computer programs with algorithms are used, taking into account special requirements. Methods that may be used for determination of identity first produce the greatest agreement between the sequences to be compared. Computer programs for determination of identity comprise, but are not restricted to, the GCG software package, including GAP (Deveroy, J. et al., 1984), and BLASTP, BLASTN and FASTA (Altschul, S. et al., 1990). The BLAST program can be obtained from the National Center for Biotechnology Information (NCBI) and from other sources (BLAST Manual, Altschul S. et al., 1990).

The well-known Smith-Waterman algorithm can also be used for determining nucleotide identity.

Parameters for nucleotide comparison may comprise the following:
Algorithm Needleman and Wunsch, 1970,
Comparison matrix
Matches=+10
Mismatches=0
Gap penalty=50
Gap length penalty=3

The GAP program is also suitable for use with the parameters given above. These parameters are usually the default parameters in the nucleotide sequence comparison.

Moreover, enzymes from the subgroup of the β-Ala: pyruvate transaminases are suitable. These include but are not limited to for example transaminases from *Pseudomonas putida* W619 (gi: 119860707, gi: 119855857, gi: 119856278), from *Pseudomonas putida* KT2440 (gi: 24984391), from *Pseudomonas aeruginosa* PA01 (gi 15595330, gi: 15600506, gi 15595418, gi 9951072); *Streptomyces coelicolor* A3(2) (gi: 3319731), *Streptomyces avermitilis* MA 4680 (gi: 29831094, gi: 29829154) and *Chromobacterium violaceum* ATCC 12472 (gi 34102747). Throughout this application, any data base code, unless specified to the contrary, refers to a sequence available from the NCBI data bases, more specifically the version online on 20 Feb. 2014, and comprises, if such sequence is a nucleotide sequence, the polypeptide sequence obtained by translating the former.

The method according to any aspect of the present invention may further comprise a step of converting the aminohexanoic acid ester to aminohexanoic acid. In particular, ω-aminohexanoic acid esters to the corresponding ω-aminohexanoic acids. The recombinant cell according to the method of the present invention may be capable of increased activity of an enzyme which catalyses the conversion of ω-aminohexanoic acid esters to the corresponding ω-aminohexanoic acids, the enzyme may be an esterase, which may be secreted by the cell. Secretion of the esterase by the cell has the advantage that the ester bond is only cleaved outside of the cell. Since the membrane permeability of the ω-aminohexanoic acid ester is better compared to the ω-aminohexanoic acid, the ω-aminohexanoic acid ester leaves the cell and enters the nutrient medium surrounding the cell. The esterases found outside of the cell will then be more efficient in metabolising the conversion of ω-aminohexanoic acid ester to ω-aminohexanoic acid.

In particular, the esterase used may be a lipase. In one example, a suitable lipase may be the lipase LipA from *Pseudomonas fluorescens* HU380 (ACC Code Q76D26, Kojima and Shimizu, 2003). In order to ensure that the esterases are secreted out of the cell, the esterases may be provided, in a manner known by a skilled person, with corresponding signal sequences, which establish secretion. If for example the lipase LipA from *Pseudomonas fluorescens* HU380 is overexpressed in *E. coli*, it can be provided advantageously with signal sequences from EstA, an esterase that occurs naturally on the cell surface of *Pseudomonas aeruginosa* (Becker et al., 2005). Other suitable enzymes are lipases from *C. antarctica, M. miehei* and *P. cepacia* (Vaysse et al., 2002).

Alternatively, the secreted ω-aminohexanoic acid ester can also be cleaved conventionally, to obtain the ω-aminohexanoic acid, for example by saponification, i.e. hydrolysis of the ω-aminohexanoic acid ester by the aqueous solution of a hydroxide, for example sodium hydroxide.

In one example, the ω-aminohexanoic acid may be converted to lactams. Lactams are cyclic amides that may form the basis for formation of polyamides. In particular, ring opening polymerisation of lactams may lead to the formation of nylon. More in particular, 6-hexanolactam may be polymerised to form nylon-6.

In the production of ω-aminohexanoic acids, ω-aminohexanoic acid esters or of lactams derived from ω-aminohexanoic acids, the following process steps are carried out:

I) contacting the recombinant cell according to any aspect of the present invention with a culture medium containing the $C_1$-$C_4$ hexanoate or with a culture medium contiguous with an organic phase containing the $C_1$-$C_4$ hexanoate in conditions that enable the cell to form ω-aminohexanoic acids, ω-aminohexanoic acid esters and/or lactams derived from ω-aminohexanoic acids, from the $C_1$-$C_4$ hexanoate; and/or II) isolation of the resultant ω-aminohexanoic acids, ω-aminohexanoic acid esters and/or lactams derived from ω-aminohexanoic acids.

The genetically modified cells used according to the method of the invention can be brought into contact with a nutrient medium, and therefore cultivated continuously or discontinuously in a batch process or in a fed-batch process or in a repeated-fed-batch process, for the purpose of producing ω-aminohexanoic acids, or lactams derived from ω-aminohexanoic acids. A semi-continuous process is also conceivable, as described in GB1009370A. Known culture methods are described in Chmiel's textbook, 1991 or in the textbook by Storhas 1994.

The culture medium to be used must be suitable for the requirements of the particular strains. Descriptions of culture media for various microorganisms are given in "*Manual of Methods for General Bacteriology*".

Organic nitrogen-containing compounds such as peptones, yeast extract, meat extract, malt extract, corn-steep liquor, soybean flour and urea or inorganic compounds such as ammonium sulphate, ammonium chloride, ammonium phosphate, ammonium carbonate and ammonium nitrate can be used as the nitrogen source. The nitrogen sources can be used separately or as a mixture.

In one example, according to any aspect of the present invention at least during the phase of formation of ω-aminohexanoic acids, ω-aminohexanoic acid esters and/or lactams derived from ω-aminohexanoic acids, the culture medium used in step I) contains amino group donors, such as ammonia or ammonium ions or even amino acids, though in particular alanine or aspartate, which function as amine donors in the transaminase-catalysed conversion of the ω-oxohexanoic acids and/or the ω-oxohexanoic acid esters to the corresponding ω-aminohexanoic acids and/or ω-aminohexanoic acid esters.

Phosphoric acid, potassium dihydrogen phosphate or dipotassium hydrogen phosphate or the corresponding sodium-containing salts can be used as the source of phosphorus. The culture medium may in addition contain salts of metals, for example magnesium sulphate and/or iron sulphate, which are required for growth. Essential growth substances such as amino acids and/or vitamins may also be used in addition to the substances mentioned above. Suitable precursors can also be added to the culture medium. The above substances can be added to the culture in the form of a single preparation, or they can be supplied in a suitable manner during cultivation.

Basic compounds such as sodium hydroxide, potassium hydroxide, ammonia, ammonia water and/or acid compounds such as phosphoric acid or sulphuric acid may be used in a suitable manner for controlling the pH of the culture. Antifoaming agents, e.g. fatty acid polyglycol esters, may be used for controlling foaming. Plasmid stability may be maintained with use of suitable antibiotics in the culture medium. Aerobic conditions may be maintained with use of oxygen or oxygen-containing gas mixtures, e.g. air, may be fed into the culture medium. The temperature of the culture may be in the range from 20° C. to 45° C. or 25° C. to 40° C.

In one example, in the method according to the invention for the production of ω-aminohexanoic acids, ω-aminohexanoic acid esters and/or lactams derived from ω-aminohexanoic acids, a recombinant cell, derived from an *E. coli* is used in a mineral salt medium supplemented with ampicillin, chloramphenicol and kanamycin according to Riesenberg et al., 1990.

In one example, in the method according to the invention, the cells are first cultivated, for the purpose of biomass production in a nutrient medium that does not contain $C_1$-$C_4$ hexanoate. It is only after a certain biomass has been obtained that the $C_1$-$C_4$ hexanoate is added to the nutrient medium and/or the cells are brought into contact with a new nutrient medium containing the $C_1$-$C_4$ hexanoate. In this regard, the amount of $C_1$-$C_4$ hexanoate present during the formation of ω-aminocarboxylic acids, ω-amino hexanoic acid esters and/or lactams derived from ω-amino hexanoic acids may be in the range from 1 to 200 g/l, especially in the range from 20 to 200 g/l.

According to one example of the present invention, the method according to the invention is carried out in a two phase system, containing an aqueous phase, and an organic phase. The formation of the ω-aminohexanoic acids, ω-aminohexanoic acid esters and/or lactams derived from ω-aminohexanoic acids by the recombinant cells in step I) takes place in the aqueous phase. The resultant ω-aminohexanoic acids, ω-aminohexanoic acid esters and/or lactams derived from ω-aminohexanoic acids accumulate in the organic phase. In this way it is possible for the resultant ω-aminohexanoic acids, ω-aminohexanoic acid esters and/or the lactams derived from (ω-aminohexanoic acids to be extracted in situ.

As organic phase, it is possible to use alkanes of medium chain length and those with a log P value of more than 4 (little foam formation), or physically similar aromatics or aromatic esters. In step II) of the method according to the invention, the resultant ω-aminohexanoic acids, ω-aminohexanoic acid esters and/or the lactams derived from the ω-aminohexanoic acids are optionally isolated, and it may for this isolation take place in a two-stage purification process, comprising a) an extraction step, in which the ω-aminohexanoic acids, ω-aminohexanoic acid esters and/or lactams derived from ω-aminohexanoic acids are extracted from the culture medium, and b) a fine purification step, in which the extract obtained in step a) is purified further by a distillation process or selective crystallization, obtaining an ω-aminohexanoic acid phase, an ω-aminohexanoic acid ester phase and/or a lactam phase with a purity of at least 99.8%.

The extraction in step a) can in particular be designed as sω-called "in situ" extraction, in which steps I) and II) of the method according to the invention for the production of ω-aminohexanoic acids, ω-aminohexanoic acid esters and/or lactams derived from ω-aminohexanoic acids are carried out simultaneously.

The fine purification in step II) can for example take place by distillation or crystallization.

In one example, the aminohexanoic ester may be converted to aminohexanoic acid using a chemically analogous procedure known in the art.

A further enzyme may catalyse the conversion of ω-aminocarboxylic acids to the corresponding lactams, and it can also be advantageous here if this enzyme is secreted by the cell. In this way it can be possible for the ω-aminocarboxylic acids formed directly by the cell or the ω-aminocarboxylic acid that is only formed after extracellular cleavage of ω-aminocarboxylic acid esters to be converted to the corresponding lactam, thus optionally facilitating purification of the target product.

In another example, the aminohexanoic acid is catalysed directly to form nylon. Nylon is the term commonly used to describe aliphatic polyamides. Common aliphatic polyamides such as nylon 6, nylon 6,6 and nylon 6,10 exhibit high mechanical strength, toughness, and chemical resistance, and can be drawn to form high-strength fibres. The nylon may be selected from the group consisting of nylon-6,6, nylon-6, nylon-6,9, nylon-6,10, and nylon-6,12. In particular, the nylon may be nylon-6,6, nylon-6, nylon-6,9, nylon-6,10 or nylon-6,12. Even more in particular, the nylon may be nylon-6. In one example there may be more than one type of nylon formed in the reaction.

Nylon may be produced from the aminohexanoic acid and/or aminohexanoic acid ester using any method known in the art. In one example, the nylon may be produced from the lactam derived from the ω-aminohexanoic acid.

The production of the polyamides from lactams can be carried out by well-known methods, as described for example in DE1495198, DE2558480, EP0129196 or also in "Polymerization Processes", 1977.

In another example, the nylon 6 may be produced directly by polycondensation of ω-aminohexanoic acid and/or lactams derived therefrom.

In particular, the nylon may be based, up to at least 10 wt. %, at least 25 wt. %, at least 50 wt. % or up to at least 75 wt. %, on ω-aminohexanoic acid, ω-aminohexanoic acid ester and/or lactam derived from the ω-aminohexanoic acid.

According to another aspect of the present invention, there is provided an aminohexanoic acid and/or aminohexanoic acid ester obtained by the method of the present invention. There may also be provided a lactam derived from the aminohexanoic acid produced according to the method of the present invention.

According to one aspect of the present invention, there is provided a method for the production of nylon based on aminohexanoic acid and/or aminohexanoic acid ester comprising:

producing an aminohexanoic acid and/or aminohexanoic acid ester by the method according to any aspect of the present invention; and polymerizing the aminohexanoic acid and/or aminohexanoic acid ester to obtain a nylon.

According to yet another aspect there is provided a nylon obtained by the method according to any aspect of the present invention.

EXAMPLES

Figure 1:
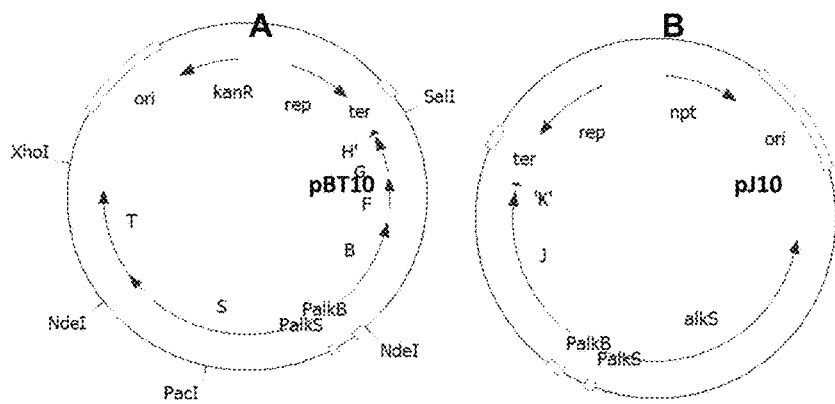
FIG. 1 shows expression vector pBT10 (A) for the alkane monooxygenase (AlkBGT) (Schrewe et al., 2011) and PJ10 (B) for the alcohol dehydrogenase AlkJ

The foregoing describes preferred embodiments, which, as will be understood by those skilled in the art, may be subject to variations or modifications in design, construction or operation without departing from the scope of the claims. These variations, for instance, are intended to be covered by the scope of the claims.

Example 1

Production of Ethanol and Acetate from Synthesis Gas

For the biotransformation of synthesis gas (66% $H_2$, 33% $CO_2$) to ethanol and acetate, the bacterium *Clostridium ljungdahlii* was used. All cultivation steps were carried out under anaerobic conditions in pressure-resistant glass bottles that can be closed airtight with a butyl rubber stopper.

For the cell culture of *C. ljungdahlii* 5 mL cryoculture was grown anaerobically in 50 ml of ATCC1754 medium (ATCC1754 medium: pH 6.0, 20 g/L MES, 1 g/L yeast extract, 0.8 g/L NaCl, 1 g/L $NH_4Cl$, 0.1 g/L KCl, 0.1 g/L $KH_2PO_4$, 0.2 g/L $MgSO_4 \cdot 7H_2O$, 0.02 g/L $CaCl_2 \cdot 2H_2O$, 20 mg/L nitrilotriacetic acid, 10 mg/L $MnSO_4 \cdot xH_2O$, 8 mg/L $(NH_4)_2Fe(SO_4)_2 \cdot 6H_2O$, 2 mg/L $CoCl_2 \cdot 6H_2O$, 2 mg/L $ZnSO_4 \cdot 7H_2O$, 0.2 mg/L $CuCl_2 \cdot 2H_2O$, 0.2 mg/L Na$_2$MoO$_4$x2H$_2$O, 0.2 mg/L NiCl$_2$x6H$_2$O, 0.2 mg/L Na$_2$SeO$_4$, 0.2 mg/L Na$_2$WO$_4$x2H$_2$O, 20 g/L d-biotin; 20 µg/L folic acid, 100 µg/L pyridoxine HCl, 50 g/L thiamine-HClxH$_2$O, 50 g/L riboflavin, 50 g/L nicotinic acid, 50 g/L calcium pantothenate, 1 g/L vitamin B12, 50 g/L p-aminobenzoate, 50 µg/L lipoic acid, about 67.5 mg/L NaOH, 400 mg/L L-cysteine hydrochloride, 400 mg/L Na$_2$Sx9 H$_2$O, 5 g/L fructose). From this culture, 10 ml was taken and inoculated in 100 ml of ATCC1754 medium to start the growth culture. This growth culture was incubated at 35° C. for 3 days.

For the production phase, the cells were harvested from the growth culture and washed with production medium. Subsequently, the cell pellet was resuspended in 75 ml of production medium (DM4 Medium: pH 5.8; 15 mg/l FeCl$_2$x4H$_2$O, 2 g/l (NH$_4$)H$_2$PO$_4$, 0.2 g/l NaCl, 0.15 g/l KCl, 0.5 mg/l Resazurin, 3 mg/l H$_3$BO$_3$, 2 mg/l CoCl$_2$x6H$_2$O, 1 mg/l ZnSO$_4$x7H$_2$O, 300 µg/l Na$_2$MoO$_4$x2H$_2$O, 300 µg/l MnSO$_4$xH$_2$O, 200 µg/l NiCl$_2$x6H$_2$O, 100 µg/L CuCl$_2$x2H$_2$O, 100 µg/l Na$_2$SeO$_3$, 106 µg/l d-Biotin, 5 µg/l Folic acid, 2.5 µg/l Pyridoxin-HCl, 266 µg/l Thiamin-HCl, 12.5 µg/l Riboflavin; 12.5 µg/l Nicotinic acid, 413 µg/l Ca-pantothenate, 12.5 µg/l Vitamin B$_{12}$, 12.5 µg/l p-aminobenzoate, 15.0 µg/l lipoic acid, 0.5 g/l MgCl$_2$x7H$_2$O, 0.2 g/l CaCl$_2$x2H$_2$O in flameproof, sterile glass bottles (volume 250 ml) and the production phase of *C. ljungdahlii* started. The production culture was capped with a butyl rubber stopper with synthesis gas (66% H$_2$, 33% CO$_2$, 1.8 bar) and left for 113.75 h and incubated at 35° C. and shaken at 100 rpm. During the cultivation, the gas phase was changed daily and samples were taken daily to determine the optical density and different analytes produced by NMR. The results showed that the amount of acetate produced increased from 0.02 g/l to 1.2 g/l and the amount of ethanol produced increased from 0.01 g/l to 0.1 g/l. Hexanoic acid and butyric acid could not be detected.

Example 2

Production of Butyric and Hexanoic Acid from Synthesis Gas

For the biotransformation of synthesis gas to butyric acid and hexanoic acid, a ω-culture of *Clostridium ljungdahlii* and *Clostridium kluyveri* was used in the production phase. The bacterium *Clostridium ljungdahlii* converted the H$_2$ and CO$_2$ from the ambient atmosphere to acetate and ethanol. These products were taken up by from the aqueous phase and converted into butyric acid and hexanoic acid by the *Clostridium kluyveri*.

All cultivation steps were carried out under anaerobic conditions in pressure-resistant glass bottles that can be closed airtight with a butyl rubber stopper.

For the cell culture of *C. ljungdahlii* 10 mL cryoculture was grown anaerobically in 100 ml of ATCC1754 medium (ATCC1754 medium: pH 6.0, 20 g/L MES, 1 g/L yeast extract, 0.8 g/L NaCl, 1 g/L NH$_4$Cl, 0.1 g/L KCl, 0.1 g/L KH$_2$PO$_4$, 0.2 g/L MgSO$_4$.7H$_2$O, 0.02 g/L CaCl$_2$x2H$_2$O, 20 mg/L nitrilotriacetic acid, 10 mg/L MnSO$_4$xH$_2$O, 8 mg/L (NH$_4$)$_2$Fe(SO$_4$)$_2$x6H$_2$O, 2 mg/L CoCl$_2$x6H$_2$O, 2 mg/L ZnSO$_4$.7H$_2$O, 0.2 mg/L CuCl$_2$x2H$_2$O, 0.2 mg/L Na$_2$MoO$_4$x2H$_2$O, 0.2 mg/L NiCl$_2$x6H$_2$O, 0.2 mg/L Na$_2$SeO$_4$, 0.2 mg/L Na$_2$WO$_4$x2H$_2$O, 20 g/L d-biotin; 20 µg/L folic acid, 100 µg/L pyridoxine HCl, 50 g/L thiamine-HClxH$_2$O, 50 g/L riboflavin, 50 g/L nicotinic acid, 50 g/L calcium pantothenate, 1 g/L vitamin B12, 50 g/L p-aminobenzoate, 50 µg/L lipoic acid, about 67.5 mg/L NaOH, 400 mg/L L-cysteine hydrochloride, 400 mg/L Na$_2$Sx9 H$_2$O, 5 g/L fructose). This growing culture was incubated at 35° C. for 2 days.

For the cell culture of *Clostridium kluyveri*, 10 mL of a continuous culture of *Clostridium kluyveri*, was grown in 100 mL of DMSZ52 medium (DSMZ52 medium: pH=6.98, 10 g/L CH$_3$COOK, 0.31 g/L K$_2$HPO$_4$, 0.23 g/L KH$_2$PO$_4$, 0.25 g/l NH$_4$Cl, 0.20 g/l MgSO$_4$x7 H$_2$O, 1 g/L yeast extract, 0.50 mg/L resazurin, 10 µl/l HCl (25%, 7.7 M), 1.5 mg/L FeCl$_2$x4H$_2$O, 70 g/L ZnCl$_2$x7H$_2$O, 100 g/L MnCl$_2$x4H$_2$O, 6 g/L H$_3$BO$_3$, 190 µg/L COCl$_2$x6H$_2$O, 2 g/L CuCl$_2$x6H$_2$O, 24 g/L NiCl$_2$x6H$_2$O, 36 g/L Na$_2$MO$_4$x2H$_2$O, 0.5 mg/L NaOH, 3 g/L Na$_2$SeO$_3$x5H$_2$O, 4 µg/L Na$_2$WO$_4$x2H$_2$O, 100 g/L vitamin B12, 80 g/L p-aminobenzoic acid, 20 g/L D(+) Biotin, 200 µg/L nicotinic acid, 100 g/L D-Ca-pantothenate, 300 µg/L pyridoxine hydrochloride, 200 µl/l thiamine—HClx2H$_2$O, 20 mL/L ethanol, 2.5 g/L NaHCO$_3$, 0.25 g/L cysteine-HClxH$_2$O, 0.25 g/L Na$_2$Sx9H$_2$O). This growing culture was incubated at 35° C. for 2 days.

For the production phase, the cells were harvested from both growth cultures separately and washed with production medium. Subsequently, the cell pellets were each resuspended in 35 ml of production medium (PETC mod. Medium: pH 6.0; 10 g/l MES, 2.4 g/l of NaCl, 3 g/l NH$_4$Cl, 0.3 g/l KCl, 0.3 g/l KH$_2$PO$_4$, 0.6 g/l MgSO$_4$.7H$_2$O, 0.12 g/l CaCl$_2$x2H$_2$O, 20 mg/l nitrilotriacetic acid, 10 mg/l MnSO$_4$xH$_2$O, 8 mg/l (NH$_4$)$_2$Fe(SO$_4$)$_2$x6H$_2$O, 2 mg/l CoCl$_2$x6H$_2$O, 2 mg/l ZnSO$_4$.7H$_2$O, 0.2 mg/l CuCl$_2$x2H$_2$O, 0.2 mg/l Na$_2$MoO$_4$x2H$_2$O, 0.2 mg/l NiCl$_2$x6H$_2$O, 0.2 mg/l Na$_2$SeO$_4$, 0.2 mg/l Na$_2$WO$_4$x2H$_2$O, 2 g/l d- biotin, 2 g/l folic acid, 10 g/l pyridoxine HCl, 5 g/l thiamine-HClxH$_2$O, 5 g/l of riboflavin, 5 g/l nicotinic acid, 5 g/l of Ca-pantothenate, 5 µg/L vitamin B12, 5 g/l p-aminobenzoate, 5 µg/l lipoic acid, 10 g/l MESNA, approximately 67.5 mg/l NaOH, 300 mg/l cysteine-HClxH$_2$O, 300 mg/l Na$_2$Sx9H$_2$O) in flameproof, sterile glass bottles (volume 250 ml) and the co-production of *C. ljungdahlii* and *C. kluyveri* started. The production culture was capped with a butyl rubber stopper with synthesis gas (66% H$_2$, 33% fully $^{13}$C-labeled CO$_2$, 1.8 bar) and left for 191 h and incubated at 35° C. and shaken at 100 rpm. During the cultivation, the gas phase was changed daily and samples were taken daily to determine the optical density and different analytes produced by NMR.

The amount of products is determined using semi-quantitative $^1$H-NMR spectroscopy of a sterile-filtered supernatant from this mixed production. The samples were in accordance with phosphate buffer diluted (in D$_2$O stated) and measured with water suppression. Measurements were carried out with and without suppression of $^{13}$C coupling. As an internal quantification standard, sodium trimethylsilyl-propionate (TSP) was used.

The results showed that the amount of acetate produced increased from 0.05 g/l to 1.7 g/l (93 mol % of the total acetate produced was $^{13}$C marked) and the amount of ethanol produced increased from 0.05 g/l to 0.12 g/l (92 mol % of the total ethanol produced was $^{13}$C marked). Also, the concentration of hexanoic acid was increased from 0.02 g/l to 0.13 g/l (63 mol % of the total hexanoic acid produced was $^{13}$C marked) and butyric acid was increased from 0.01 g/l to 0.07 g/l (63 mol % of the total butyric acid produced was $^{13}$C marked). This confirmed that a large percentage of the hexanoic acid and butyric acid produced derived from the C source of the synthesis gas.

Example 3

Production of Hexanoic Acid and Butyric Acid from Ethanol and Acetate

For the biotransformation of ethanol and acetate to hexanoic acid and butyric acid the bacterium *Clostridium kluyveri* was used. All cultivation steps were carried out under anaerobic conditions in pressure-resistant glass bottles that can be closed airtight with a butyl rubber stopper.

A cyroculture of *Clostridium* in 5 ml of DMSZ52 medium (DSMZ52 medium: pH=6.98, 10 g/L $CH_3COOK$, 0.31 g/L $K_2HPO_4$, 0.23 g/L $KH_2PO_4$, 0.25 g/l $NH_4Cl$, 0.20 g/l $MgSO_4 \times 7\ H_2O$, 1 g/L yeast extract, 0.50 mg/L resazurin, 10 µl/l HCl (25%, 7.7 M), 1.5 mg/L $FeCl_2 \times 4H_2O$, 70 µg/L $ZnCl_2 \times 7H_2O$, 100 µg/L $MnCl_2 \times 4H_2O$, 6 µg/L $H_3BO_3$, 190 µg/L $COCl_2 \times 6H_2O$, 2 µg/L $CuCl_2 \times 6H_2O$, 24 µg/L $NiCl_2 \times 6H_2O$, 36 µg/L $Na_2MO_4 \times 2H_2O$, 0.5 mg/L NaOH, 3 µg/L $Na_2SeO_3 \times 5H_2O$, 4 µg/L $Na_2WO_4 \times 2H_2O$, 100 g/L vitamin B12, 80 g/L p-aminobenzoic acid, 20 g/L D(+) Biotin, 200 µg/L nicotinic acid, 100 µg/L D-Ca-pantothenate, 300 µg/L pyridoxine hydrochloride, 200 µl/L thiamine—HClx$2H_2O$, 20 mL/L ethanol, 2.5 g/L $NaHCO_3$, 0.25 g/L cysteine-HClx$H_2O$, 0.25 g/L $Na_2Sx9H_2O$) was placed in a 250 ml bottle and 50 ml of DSMZ52 medium added. This growing culture was incubated at 35° C. for 3 days. Then 100 ml of DSMZ52 medium was inoculated with 10 ml of this culture to produce a preparatory culture. This preparatory culture was incubated at 35° C. for 3 days. For production of a main culture, 200 ml of DSMZ52 medium was inoculated with 5% of the cells from the preparatory culture in 500 ml bottles. The culture was capped with a butyl rubber stopper and incubated for 98 h and incubated at 35° C. At the start and end of the culturing period, samples were taken. These were tested for optical density and the different analytes by NMR. There was a growth of $OD_{600}$~0.01 to a maximum of 0.35 to 0.37. The results showed that the amount of acetate decreased from 4.9 g/l to 2.4 g/l and the amount of ethanol decreased from 12.5 g/l to 9.2 g/l. Also, the concentration of hexanoic acid was increased from 0.1 g/l to 6.85 g/l and butyric acid was increased from 0.1 g/l to 2.9 g/l.

Example 4

The Formation of Hexanoic Acid from Synthesis Gas Using *C. carboxidivorans*

The wild-type strain *Clostridium carboxidivorans* (Accession No. DSM 15243) were obtained from DSMZ (Deutsche Sammlung von Mikroorganismen und Zellkulturen GmbH) and cultivated autotrophically to form hexanoic acid from synthesis gas. All cultivation steps were carried out under anaerobic conditions in pressure-resistant glass bottles that can be closed airtight with a butyl rubber stopper.

A complex medium was used to grow the cells. The complex medium was made of: 3 g/l $NH_4Cl$, 0.3 g/l KCl, 0.6 g/l $MgSO_4 \times 7H_2O$, 2.4 g/l NaCl, 0.3 g/l $KH_2PO_4$, 120 mg/l $CaCl_2 \times 2\ H_2O$, 10 g/l MES, 1 g/l yeast extract, 0.4 g/l L-Cysteine-HCl, 20 mg/l nitrilotriacetic acid, 10 mg/l $MnSO_4 \times H_2O$, 8 mg/l $(NH_4)_2Fe(SO_4)_2 \times 6H_2O$, 2 mg/l $CoCl_2 \times 6H_2O$, 2 mg/l $ZnSO_4 \times 7H_2O$, 0.2 mg/l $CuCl_2 \times 2H_2O$, 0.2 mg/l $Na_2MoO_4 \times 2H_2O$, 0.2 mg/l $NiCl_2 \times 6H_2O$, 0.2 mg/l $Na_2SeO_4$, 0.2 mg/l $Na_2WO_4 \times 2H_2O$, 20 µg/l d-Biotin, 20 µg/l folic acid, 100 µg/l Pyridoxin-HCl, 50 µg/l Thiamin-HClx$H_2O$, 50 µg/l Riboflavin, 50 µg/l nicotinic acid, 50 µg/l Ca-pantothenate, 50 µg/l Vitamin $B_{12}$, 50 µg/l p-aminobenzoate, 50 µg/l lipoic acid, 100 µg/l MESNA pH 6.0.

An autotrophic cultivation was carried out in a 1 L-septum bottle filled with 500 ml of the complex medium and the *Clostridium carboxidivorans* strain. The incubation was performed at 37° C. with a shaking frequency of 100 min$^{-1}$ in an open water bath shaker (Innova 3100 by New Brunswick Scientific). The gas trapped in the medium was removed by a sparger with a pore size of 10 microns, which was mounted in the center of the reactors. Culturing is carried out with no pH control. The reactors were purged with a premixed gas mixture of composition 67% $H_2$, 33% $CO_2$ at atmospheric pressure with an aeration rate of 3 I/h (0.1 vvm) through the sparger.

The reactor started with 5 ml of a cryoculture of *Clostridium carboxidivorans* inoculated in glycerol (10%) that was heterotrophic with fructose in the absence of $O_2$ in the abovementioned complex medium. The culture was and incubated for 46 h and incubated at 35° C.

When obtaining samples, 5 ml of each sample as taken for determination of $OD_{600}$, pH and the product spectrum. The determination of the product concentration was performed by semi-quantitative $^1$H-NMR spectroscopy. As an internal quantification standard sodium trimethylsilylpropionate (T(M)SP) was used.

The results showed an increase in $OD_{600}$ of 0.01 to 0.18 with a decrease in pH from 5.75 to 5.51. Also, the acetate concentration decreased from 7 mg/l to 0.8 g/l, the ethanol concentration increased from 0 g/l to 0.16 g/l and the butyrate concentration increased from 0 to 0.19 g/l. Also, 63 mg/l of hexanoic acid was formed during this period.

Example 5

*E. coli* JM101 (pBT10) as Whole Cell Catalyst for Oxidation of Methyl Hexanoate and/or Hydroxymethyl Hexanoate A recombinant *E. coli* strain JM101 cells which carry the plasmid pBT10 (FIG. 1A) expressing the three genes alkane hydroxylase (AlkB), rubredoxin (AlkG) and rubredoxin reductase (AlkT) from *Pseudomonas putida* were produced according to Schrewe et al., 2011 and WO02009077461A1.

In summary, the following steps were carried out.

Construction of the alkBGT Expression Vectors

The construct pBT10 (FIG. 1A, SEQ ID NO: 1), which contains the three components alkane hydroxylase (AlkB), rubredoxin (AlkG) and rubredoxin reductase (AlkT) from *Pseudomonas putida* that are necessary for the oxidation to the aldehyde, was produced starting from the pCOM systems (Smits et al., 2001). For expression of the three genes, the alkBFG gene sequence was put under the control of the alkB-promoter and the alkT gene under the control of the alkS-promoter (SEQ ID NO:9).

Cloning Strategy

To simplify the cloning of alkB and alkG, the gene alkF located between them was amplified and cloned together with alkB and alkG. AlkF is of no significance for the reaction that is to be catalysed.

PCR amplification of the fragment alkBFG=2524 bp (cf. SEQ ID NO:2 (alkB) and SEQ ID NO:3 (alkG) with NdeI cleavage site upstream of alkB and SaiI cleavage site downstream of alkG. The sequences of the primers are provided in Table 2 below.

PCR amplification of the fragment alkT (2958 bp) (SEQ ID NO:4 (alkT))

TABLE 2

Primers used to amplify alkBFG and alkT

| SEQ ID NO | Sequence | Description |
|---|---|---|
| 5 | AAGGGAATTCCATATGCTTG AGAAACACAGAGTTC | alkBFG forward |
| 6 | AAAATTCGCGTCGACAAGCG CTGAATGGGTATCGG | alkBFG reverse |
| 7 | TGAGACAGTGGCTGTTAGAG | alkT forward |
| 8 | TAATAACCGCTCGAGAACGC TTACCGCCAACACAG | alkT reverse |

Figure 8:
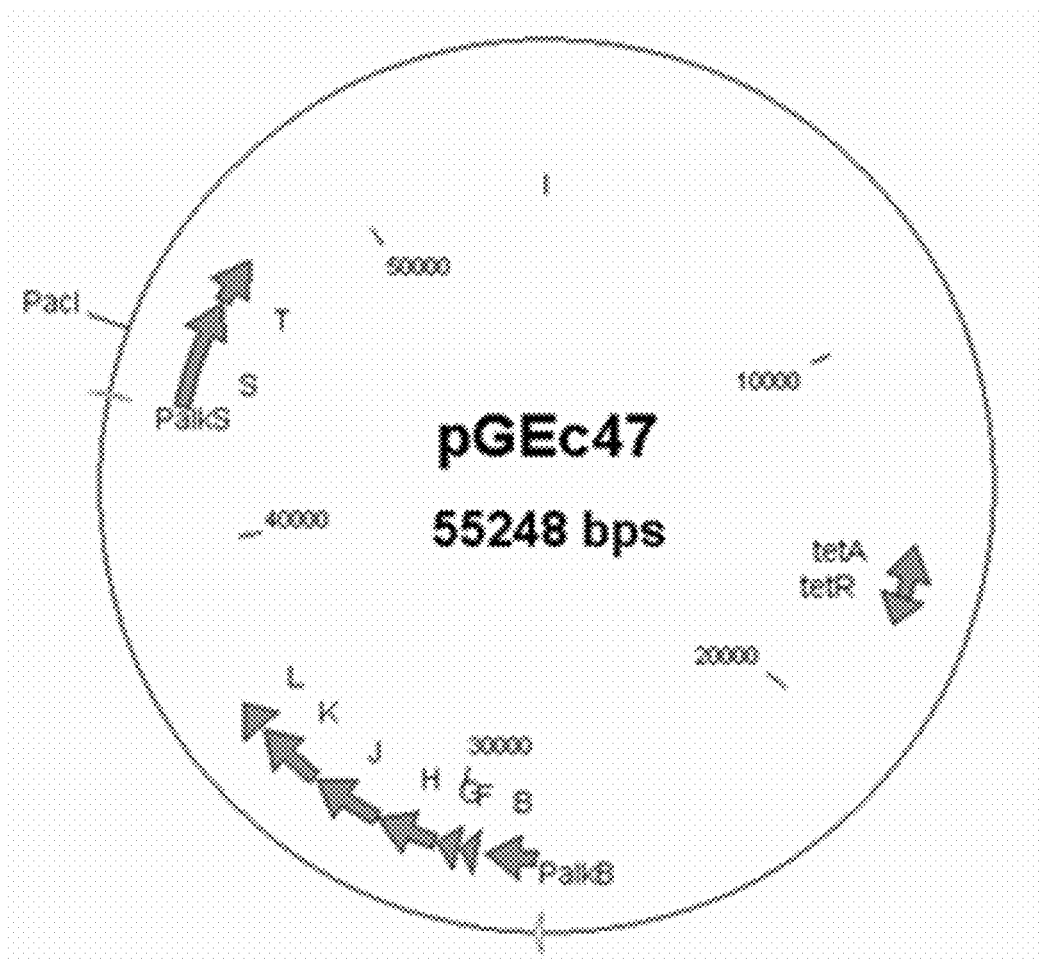
FIG. 8 shows the starting plasmid pGEc47, which was used as template for the amplification of alkBGTS.

The fragments alkBFG and alkT were amplified by PCR. The plasmid pGEc47 (FIG. 8) (Eggink et al. (1987)) was used as template.

Figure 9:
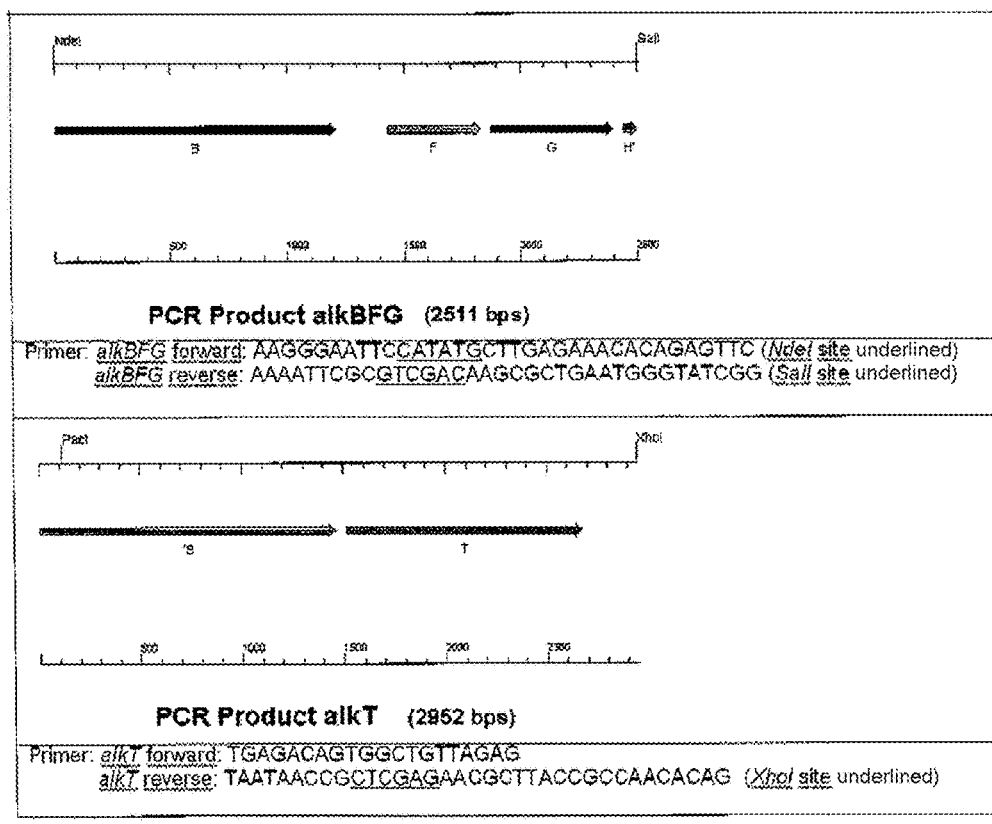
FIG. 9 shows the primers used and the resultant PCR products alkBFG and alkT. The primer sequences shown in the figure are as follows: alkBFG forward is SEQ ID NO:5; alkBFG reverse is SEQ ID NO:6; alkT forward is SEQ ID NO:7 and alkT reverse is SEQ ID NO:8.

The cloning was carried out by means of the subcloning vector pSMART® HCKan (Lucigen Corporation) which was already linearized and provided with blunt ends, and was ligated with the respective blunt-end PCR product (FIG. 9).

Next, the alkBFG fragment with the restriction enzymes NdeI and SaII and the alkT fragment with the restriction enzymes PacI and XhoI were cut out of the subcloning vectors. The fragments were separated in agarose gel (1%), cut out of the gel and isolated using a gel extraction kit.

The fragments were ligated one after another into the vector pCOM10 (Smits, T. H. M. et. al., 2001). In the first step alkBFG was inserted in pCOM10 via the cleavage sites NdeI and SaII, and in a second step alkT was then cloned via the cleavage sites PacI and XhoI.

The recombinant plasmid was transformed in *E. coli* DH$_5\alpha$. Plasmid-bearing clones were selected on kanamycin-containing LB medium. The isolated plasmid was checked by restriction analysis and sequencing. It is designated pBT10 (FIG. 1A). For the biotransformation, the plasmid pBT10 was transformed by heat shock at 42° C. for 2 min in the chemically competent strain *E. coli* JM101.

All cell assays were carried out using the following conditions:

The *E. coli* strain JM101 cells were grown at 30° C. in M9 medium (composition: 6.8 g/l Na$_2$PO$_4$.2H$_2$O, 2.4 g/l KH$_2$PO$_4$, 0.4 g/l NaCl, 1.6 g/l NH$_4$Cl, 0.5 g/l MgSO$_4$.7H$_2$O, 1 ml of trace element solution US3, consisting of 36.5 g/l of 37% strength hydrochloric acid, 1.91 g/l MnCl$_2$.4H$_2$O, 1.87 g/l ZnSO$_4$.7H$_2$O, 0.84 g/l Na-EDTA.2H$_2$O, 0.3 g/l H$_3$BO$_3$, 0.25 g/l Na$_2$MoO$_4$.2H$_2$O, 4.7 g/l CaCl$_2$.2H$_2$O, 17.3 g/l FeSO$_4$.7H$_2$O, 0.15 g/l CuCl$_2$.2H$_2$O). Inoculation was done when the OD$_{450}$=0.2. The cells were left to grow and when OD$_{450}$ reached 0.5, induction of gene expression was carried out with 0.025% (v/v) dicyclopropylketone (DCPK), a potent gratuitous inducer of alkane hydroxylase activity. The cells were incubated for a further 4 hours. The cells were then harvested by centrifugation, the cell pellet was resuspended in 50 mM potassium phosphate buffer (KPi, pH 7.4 containing 1% (w/v) glucose and put in a bioreactor. The growth was stopped with 40 µl of 10% (v/v) perchloric acid which allows for protonation to the resulting acid and thus makes the extraction of the reaction mixture by ether feasible.

The reaction mixture was then extracted by diethyl ether and subsequent quantification of the substrate and product concentrations carried out by gas chromatography. Each of the recombinant cells was contacted with methyl hexanoate separately in a resting cell assay and samples taken over a longer period.

Figure 2:
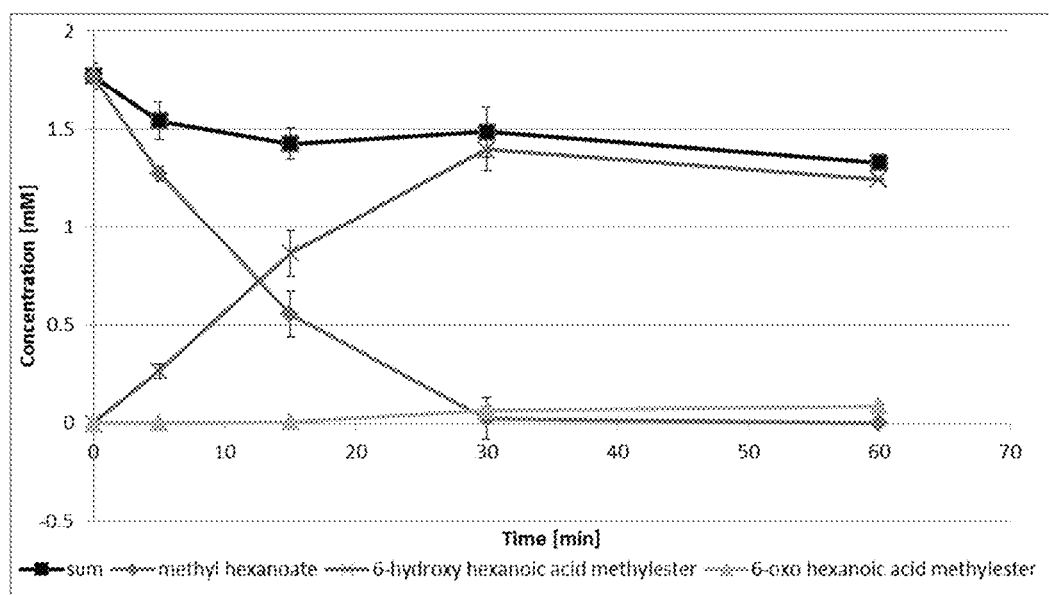
FIG. 2 is a graph showing the whole cell reaction (hydroxylation) of hexanoic acid to methyl hexanoate with *E. coli* JM101 (pBT10) by measuring the total concentration of methyl hexanoate, 6-hydroxy methylhexanoate (6 hydroxy hexanoic acid methylester) and oxomethyl hexanoate (6-oxo hexanoic acid methylester). Biomass concentration: 0.68±0.02 $g_{CDW}$ $L^{-1}$ in KPi-buffer (pH 7.4) containing 1% (w/v) glucose. Data was each measured in duplicates from two biological replicates.
Figure 3:
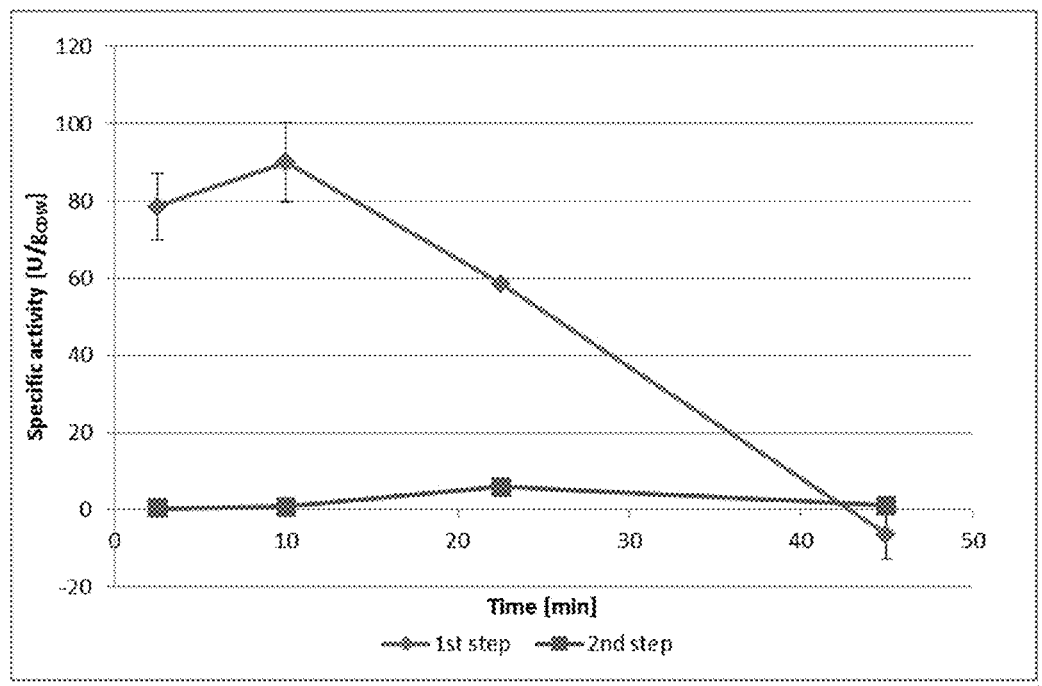
FIG. 3 is a graph showing the measurement of specific activity in the whole cell reaction where step 1 is the measurement of hydroxylation of hexanoic acid to methyl hexanoate with *E. coli* JM101 (pBT10) and step 2 is the measurement of the alcohol oxidation step. Biomass concentration: 0.68±0.02 $g_{CDW}$ $L^{-1}$ in KPi-buffer (pH 7.4) containing 1% (w/v) glucose. Data was each measured in duplicates from two biological replicates.

Resting *E. coli* JM101 (pBT10) catalysed the conversion of methyl hexanoate to hydroxymethyl hexanoate efficiently as shown in FIGS. 2 and 3. The AlkBGT-catalysed oxidation of hydroxymethyl hexanoate to oxomethyl hexanoate occurred only to a small extent.

As can be seen in Table 3 below, the maximum specific activity for the hydroxylation reaction (first step) was shown to be approximately 90 U g$_{CDW}$ and for the alcohol oxidation step (second step) was shown to be 6 U g$_{CDW}$.

Figure 4:
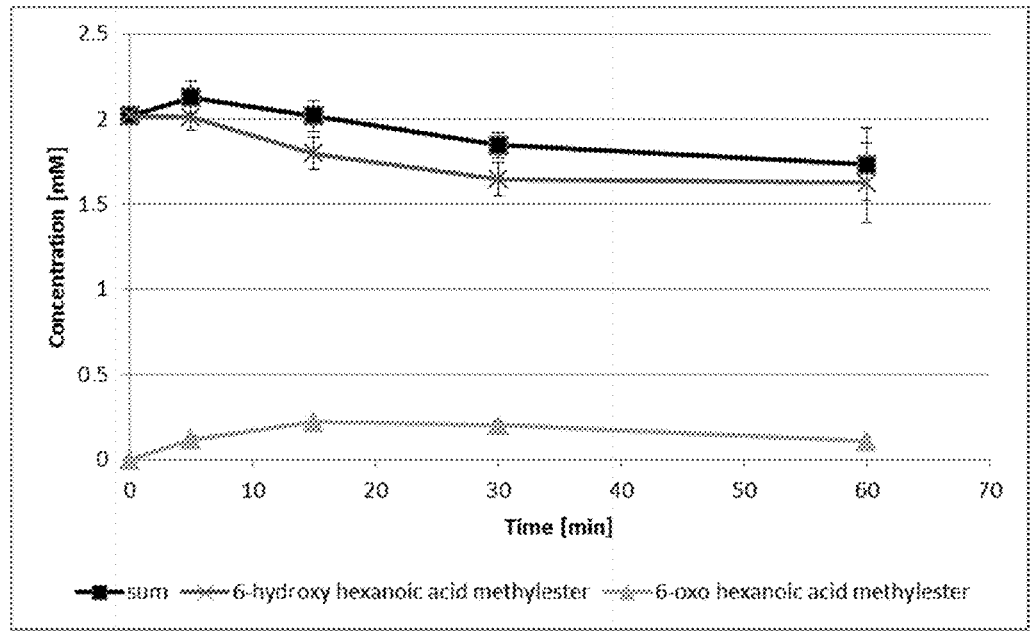
FIG. 4 is a graph showing the whole cell reaction of 6-hydroxy methylhexanoate to oxomethyl hexanoate with *E. coli* JM101 (pBT10) by measuring the total concentration of 6-hydroxy methylhexanoate (6 hydroxy hexanoic acid methylester) and oxomethyl hexanoate (6-oxo hexanoic acid methylester). Biomass concentration: 0.86 $g_{CDW}$ $L^{-1}$ in KPi-buffer (pH 7.4) containing 1% (w/v) glucose. Data was each measured in duplicates from two biological replicates.
Figure 5:
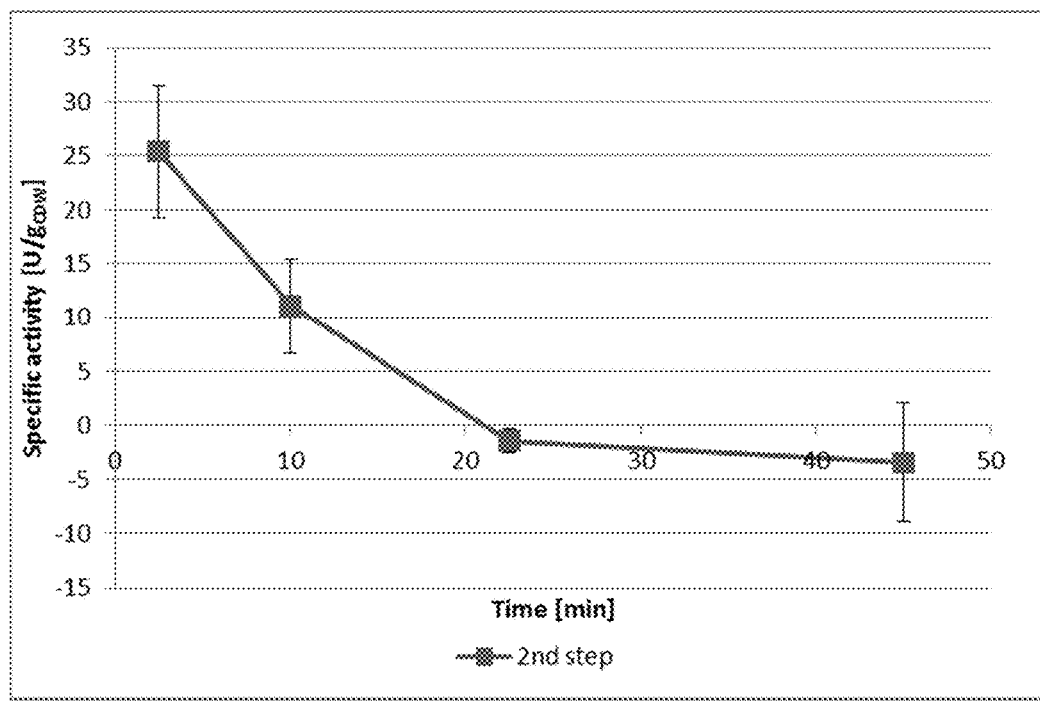
FIG. 5 is a graph showing the measurement of specific activity in the whole cell reaction of the alcohol oxidation step (6-hydroxy methylhexanoate (6 hydroxy hexanoic acid methylester) and oxomethyl hexanoate (6-oxo hexanoic acid methylester). Biomass concentration: 0.86 $g_{CDW}$ $L^{-1}$ in KPi-buffer (pH 7.4) containing 1% (w/v) glucose. Data was each measured in duplicates from two biological replicates.

When hydroxymethyl hexanoate was used as a substrate for *E. coli* JM101 (pBT10), there was a slow and inefficient AlkBGT-catalyzed oxidation of alcohol hydroxymethyl hexanoate to oxomethyl hexanoate. A similar behaviour was observed when hydroxymethyl hexanoate was used as a substrate for *E. coli* JM101 (pBT10) as shown in FIGS. 4 and 5. A highest hydroxymethyl hexanoate oxidation rate of 25 U g$_{CDW}$ was measured and oxomethyl hexanoate accumulation stopped after 15 minutes, although significant amounts of substrate were still present. This showed that AlkBGT is not efficient in oxidation of alcohol hydroxymethyl hexanoate to oxomethyl hexanoate.

Example 6

*E. coli* JM101 (pJ10) as Whole Cell Catalyst for Oxidation of Hydroxymethyl Hexanoate The alkane hydroxylase system alkBGT from *Pseudomonas putida* GPo1 is used for the hydroxylation of hexanoic acid or of methyl hexanoate. The second step to the aldehyde is catalysed by the alcohol dehydrogenase alkJ.

A second recombinant *E. coli* strain JM101 cells which carry the plasmid pJ10 expressing the gene encoding for the alcohol dehydrogenase AlkJ from *P. putida* (FIG. 1 B) were produced.

Figure 6:
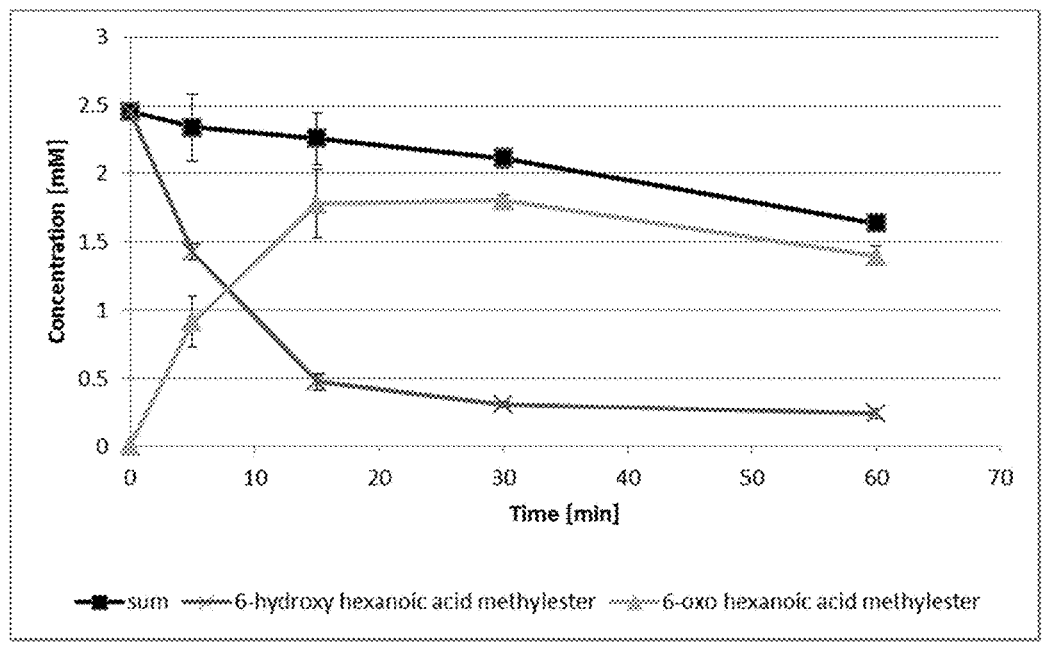
FIG. 6 is a graph showing the whole cell reaction of 6-hydroxy methylhexanoate to oxomethyl hexanoate with *E. coli* JM101 (pJ10) by measuring the total concentration of 6-hydroxy methylhexanoate (6 hydroxy hexanoic acid methylester) and oxomethyl hexanoate (6-oxo hexanoic acid methylester). Biomass concentration: 0.91 $g_{CDW}$ $L^{-1}$ in KPi-buffer (pH 7.4) containing 1% (w/v) glucose. Data was each measured in duplicates from two biological replicates.
Figure 7:
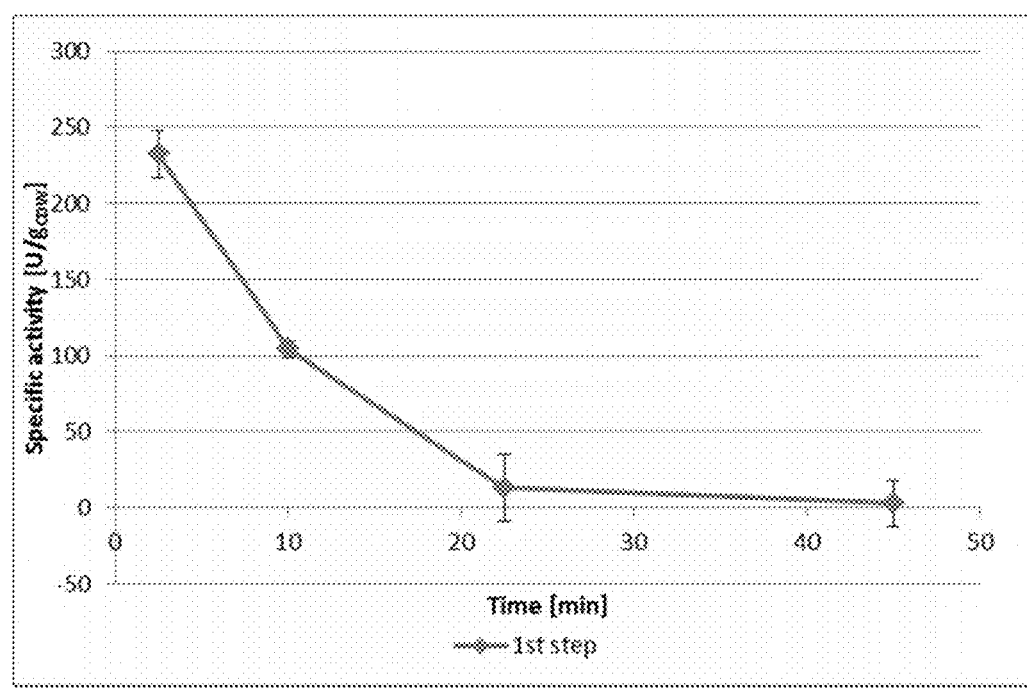
FIG. 7 is a graph showing the measurement of specific activity in the whole cell reaction of hydroxylation of 6-hydroxy methylhexanoate to oxomethyl hexanoate with *E. coli* JM101 (pJ10). Biomass concentration: 0.91 $g_{CDW}$ $L^{-1}$ in KPi-buffer (pH 7.4) containing 1% (w/v) glucose. Data was each measured in duplicates from two biological replicates.

A more efficient hydroxymethyl hexanoate oxidation was achieved by the introduction of the alcohol dehydrogenase AlkJ in *E. coli* JM101. The oxidising ability of *E. coli* JM101 (pJ10) carrying AlkJ was examined in resting cell assays. Hydroxymethyl hexanoate was used as a substrate and the results shown in FIGS. 6 and 7. As shown in Table 3 below, the measurement of hydroxymethyl hexanoate oxidation was more than 200 U g$_{CDW}$. These results showed that AlkJ catalyses the oxidation of alcohols, and is more efficient than AlkBGT in catalysing this reaction. AlkJ is thus an important component in the development of a whole cell catalyst for the production of 6-aminohexanoicmethyl ester via 6-oxoaminohexanoicmethyl ester.

TABLE 3

Measurement of maximum specific activity in the production of methyl hexanoate and 6-hydroxymethylhexanoate with resting *E. coli* JM101 (pBT10) and *E. coli* JM101 (pJ10). Biomass concentration 0.68-0.91 g$_{CDW}$ L$^{-1}$ in KPi-buffer (pH 7.4) containing 1% (w/v) glucose

| Plasmid | Substrate | Step 1 [U/g$_{CDW}$] | Step 2 [U/g$_{CDW}$] |
|---|---|---|---|
| pBT10 | Hexanoic acid methylester | 90 ± 10 | 6 ± 2 |
|  | 6-Hydroxyhexanoicmethylester | — | 25 ± 2 |
| pJ10 | 6-Hydroxyhexanoicmethylester | — | 232 ± 39 |

For efficient oxidation of the alcohol to the aldehyde, the presence of AlkJ appeared to be necessary.

REFERENCES

Altschul, S. et al., Journal of Molecular Biology 215 (1990), pages 403-410
Barker H. A., HARVEY LECT THE HARVEY LECTURES HARVEY LECTURES, Series 45/242-59 1949,
Barz et al. Plant Science, Vol. 155, pages 101-108 (2000).
Becker et al., FEBS Letters, Vol. 579, pages 1177-1182 (2005)
"*Bioprozesstechnik* 1. *Einfuhrung in die Bioverfahrenstechnik*" [Bioprocess Techniques 1. Introduction to Bioprocess Engineering] (Gustav Fischer Verlag, Stuttgart, 1991)
Bornstein B. T., et al., J. Biol. Chem. 1948, 172:659-669.
Byoung, S. J. et al., Enzyme and Microbial Technology 53 (2013) 143-151
de Lorenzo et al., J Bacteriol., Vol. 172 (11), pages 6568-6572 and 6557-6567 (1990)
Deveroy, J. et al., Nucleic Acid Research 12 (1984), page 387, Genetics Computer Group University of Wisconsin, Madison (Wis.)
Ding H. et al, Bioresource Technology 101 (2010) 9550-9559,
Drake et al., 2004. Strict and Facultative Anaerobes: Medical and Environmental Aspects. pp. 251-281, Horizon Scientific Press, United Kingdom
Drake & Kusel, 2005 Acetogenic *clostridia*. In: Durre, P. (ed.), Handbook on *Clostridia*, pp. 719-746. CRC Press, Boca Raton, Fla.
Drake et al., 2006, Acetogenic prokaryotes. In: Balows A, Truper H G, Dworkin M, Harder W and Gerhardt, P et al (ed) American Society for Microbiology, Washington, D.C. p. 248-277
Eggink et al. (1987) J. Biol. Chem. 262, 17712-17718
Kaulmann et al., 2007; *Enzyme and Microbial Technology*, Vol. 41, pages 628-637
Kieun C., Appl Biochem Biotechnol (2013) 171:1094-1107
Kojima and Shimizu, Journal of Bioscience and Bioengineering, Volume 96 (3), pages 219-226 (2003). "*Manual of Methods for General Bacteriology*" of the American Society for Bacteriology (Washington D.C., USA, 1981)
Needleman and Wunsch, Journal of Molecular Biology 48 (1970), pages 443-453
Panke et al., Appl and Environm. Microbiol., pages (1999) 5619-5623
"*Polymerization Processes*", Interscience, New York, 1977, pages 424-467, especially pages 444-446.
Reed, T B, 1981, Biomass gasification: principles and technology, Noves Data Corporation, Park Ridge, N.J.
Riesenberg, D *Appl Microbiol and Biotechnololgy*, Vol. 34 (1), pages 77-82 (1990)
Seedorf, H. et al. (2008): In: Proc Natl Acad Sci USA. 105(6); 2128-2133
Smits, T. H. M., Seeger, M. A., Witholt, B. & van Beilen, J. B. (2001) Plasmid 46, 16-24
Stadtman E. R., et al., J. Biol. Chem. 1950, 184:769-794
Steinbusch K. J. J, et al, Energy Environ. Sci., 2011, 4, 216-224
Storhas ("*Bioreaktoren und periphere einrichtungen*" [Bioreactors and Peripheral Equipment], Vieweg Verlag, Brunswick/Wiesbaden, 1994).
van Beilen et al. Journal of Bacteriology, Vol. 184 (6), pages 1733-1742 (2002)
van Beilen et al. in "*Oil & Gas Science and Technology*", Vol. 58 (4), pages 427-440 (2003)
Van Eerten-Jansen, M. C. A. A et al., ACS Sustainable Chem. Eng. 2013, 1, 513-518
Vaysse et al., "*Enzyme and Microbial Technology*", Vol. 31, pages 648-655 (2002)).
Wood, 1991 Life with CO or CO2 and H2 as a source of carbon and energy. FASEB J. 5:156-163
Zhang, F., et al., Water Research (2013)
WO98/00558, WO 00/68407, ATCC 49587, ATCC 55988 and ATCC 55989, WO2009/077461, EP0748797, U.S. 2007/0275447, U.S. 2008/0057554, WO00/20566, US2007/0092957, GB1009370A, DE1495198, DE2558480, EP0129196

The invention claimed is:

1. A method of producing 6-aminohexanoic acid and/or 6-aminohexanoic acid ester from synthesis gas, the method comprising:
  A. contacting the synthesis gas with:
    (i) at least one bacteria capable of carrying out both the Wood-Ljungdahl pathway and the ethanol-carboxylate fermentation to produce hexanoic acid; or
    (ii) at least one bacteria capable of carrying out the Wood-Ljungdahl pathway and at least a second bacteria capable of carrying out ethanol-carboxylate fermentation to produce hexanoic acid; and
  B. contacting the hexanoic acid with a genetically modified cell to produce 6-aminohexanoic acid and/or 6-aminohexanoic acid ester, wherein, in comparison with its wild type, the genetically modified cell has increased activity, of all three enzymes: alkane monooxygenase, alcohol dehydrogenase, and ω-transaminase, wherein the alcohol dehydrogenase is encoded by an AlkJ gene (EC 1.1.99-2).

2. The method of claim 1, further comprising the step of esterification of the hexanoic acid of step A to produce a C1-C4 hexanoate and wherein the C1-C4 hexanoate is contacted with the genetically modified cell of step B.

3. The method of claim 2, wherein the step of esterification involves contacting the hexanoic acid of step A with at least one C1-C4 alcohol to produce C1-C4 hexanoate.

4. The method of claim 2, wherein the step of esterification is catalysed by at least one esterification bacteria.

5. The method of claim 1, wherein in the genetically modified cell of step B,
  a) the enzyme alkane monooxygenase is encoded by the AlkBGT gene from *Pseudomonas putida*;
  b) the enzyme alcohol dehydrogenase is encoded by the AlkJ gene from *Pseudomonas putida*; and/or
  c) the enzyme ω-transaminase is the ω-transaminase CV2025 from *Chromobacterium violaceum* DSM30191.

6. The method of claim 1, further comprising a step of converting the 6-aminohexanoic acid ester to 6-aminohexanoic acid.

7. The method of claim 6, wherein the conversion of the 6-aminohexanoic acid ester to the 6-aminohexanoic acid is catalysed by lipase LipA from *Pseudomonas fluorescens*.

8. The method of claim 1, wherein the cell of step B is selected from the group consisting of: a genetically modified *Escherichia coli* cell, a genetically modified *Corynebacterium glutamicum* cell and a genetically modified *Pseudomonas putida* cell.

9. The method of claim 1, wherein the bacteria capable of carrying out the ethanol-carboxylate fermentation is selected from the group consisting of *Clostridium kluyveri* and *C. Carboxidivorans*.

10. The method of claim 3, wherein the C1-C4 alcohol is methanol.

11. The method of claim 3, wherein the hexanoic acid produced from the synthesis gas is first extracted before being contacted with the C1-C4 alcohol to produce C1-C4 hexanoate.

12. The method of claim 1, wherein the cell is in a culture medium comprising amino acids, which function as amine donor for step B.

13. The method of claim 1, wherein the 6-aminohexanoic acid is catalysed to form nylon.

14. The method of claim 13, wherein the nylon is nylon-6,6.

15. The method of claim 1, wherein the bacteria capable of carrying out the Wood-Ljungdahl pathway in step A is an acetogenic bacteria selected from the group consisting of: *Acetoanaerobium notera, Acetonema longum, Acetobacterium carbinolicum, Acetobacterium malicum, Acetobacterium* species no. 446, *Acetobacterium wieringae, Acetobacterium woodii, Alkalibaculum bacchi, Archaeoglobus fulgidus, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium glycolicum, Clostridium ljungdahlii, Clostridium ljungdahlii* C-01, *Clostridium ljungdahlii* ERI-2, *Clostridium ljungdahlii* 0-52, *Clostridium mayombei, Clostridium methoxybenzovorans, Clostridium ragsdalei, Clostridium scatologenes, Clostridium species, Desulfotomaculum kuznetsovii, Desulfotomaculum thermobezoicum* subsp. *thermosyntrophicum, Eubacterium limosum, Methanosarcina acetivorans* C2A, *Moorella* sp. HUC22-1, *Moorella thermoacetica, Moorella thermoautotrophica, Oxobacter pfennigii, Sporomusa aerivorans, Sporomusa ovata, Sporomusa silvacetica, Sporomusa sphaeroides, Sporomusa termitida*, and *Thermoanaerobacter kivui*.

* * * * *